United States Patent
Lu et al.

(10) Patent No.: US 10,668,161 B2
(45) Date of Patent: Jun. 2, 2020

(54) THERAPEUTIC HYPERBRANCHED POLYGLYCEROL ENCAPSULATED BIOMOLECULES

(71) Applicant: THE REGENTS OF THE UNIVERSITY OF CALIFORNIA, Oakland, CA (US)

(72) Inventors: Yunfeng Lu, Culver City, CA (US); Juanjuan Du, Los Angeles, CA (US); Jie Li, Los Angeles, CA (US); Yang Liu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/120,899

(22) PCT Filed: Feb. 23, 2015

(86) PCT No.: PCT/US2015/017055
§ 371 (c)(1),
(2) Date: Aug. 23, 2016

(87) PCT Pub. No.: WO2015/127347
PCT Pub. Date: Aug. 27, 2015

(65) Prior Publication Data
US 2016/0361425 A1 Dec. 15, 2016

Related U.S. Application Data

(60) Provisional application No. 61/943,788, filed on Feb. 24, 2014.

(51) Int. Cl.
| | |
|---|---|
| *A61K 47/00* | (2006.01) |
| *A61K 47/48* | (2006.01) |
| *A61K 38/51* | (2006.01) |
| *A61K 38/43* | (2006.01) |
| *A61K 47/59* | (2017.01) |
| *A61K 47/60* | (2017.01) |
| *A61K 38/44* | (2006.01) |

(52) U.S. Cl.
CPC ........ *A61K 47/48215* (2013.01); *A61K 38/43* (2013.01); *A61K 38/443* (2013.01); *A61K 38/51* (2013.01); *A61K 47/59* (2017.08); *A61K 47/593* (2017.08); *A61K 47/595* (2017.08); *A61K 47/60* (2017.08); *C12Y 101/03013* (2013.01); *C12Y 403/01024* (2013.01)

(58) Field of Classification Search
CPC .... C12Y 403/01024; C12Y 101/03013; A61K 38/43; A61K 38/443; A61K 38/51; A61K 47/48215; A61K 47/48192; A61K 47/482; A61K 47/48207; A61K 47/59; A61K 47/593; A61K 47/595; A61K 47/60
See application file for complete search history.

(56) References Cited

U.S. PATENT DOCUMENTS

| | | | | |
|---|---|---|---|---|
| 4,450,153 | A * | 5/1984 | Hopkins | A61K 38/443 424/94.4 |
| 8,519,189 | B2 | 8/2013 | Kizhankkedathu et al. | |
| 2006/0039691 | A1 | 2/2006 | Malik et al. | |
| 2006/0204472 | A1 | 9/2006 | Paleos et al. | |
| 2011/0027255 | A1* | 2/2011 | Ferrari | A61K 38/47 424/94.61 |
| 2012/0020951 | A1* | 1/2012 | Shepard | A61K 31/37 424/130.1 |
| 2013/0122112 | A1* | 5/2013 | Burt | A61K 9/5146 424/649 |

OTHER PUBLICATIONS

Calderon et al. Biochime (2010) 92: 1242-1251 (Year: 2010).*
Rossi et al. Biomaterials (2010) 31: 4167-4178 (Year: 2010).*
Wurm et al. Biomacromolecules (2012) 13: 1161-117 (Year: 2012).*
Akin et al. Biotechnol. Prog. (2009): 26(3): 896-906 (Year: 2009).*
PCT International Search Report and Written Opinion in connection with PCT/US2015/017055, dated Jul. 28, 2015.
Haxton et al. Hyperbranched Polymers for Controlled Release of Cisplatin: Electronic Supplementary informaton for Dalton Transactions, Royal Society of Chemistry 2008 [retrieved on Jun. 24, 2015]; Retrieved from the internet URL: http://www.rsc.org/suppdata/dt/b8/b809949a.pdf.

* cited by examiner

*Primary Examiner* — Susan M Hanley
(74) *Attorney, Agent, or Firm* — Quarles & Brady LLP

(57) ABSTRACT

Methods for modifying therapeutic agents such as therapeutic biomolecules, such as proteins for improved oral, rectal or transmucosal delivery, as well as compositions made using such methods and methods of administering such compositions to a subject, are disclosed. Specifically, the therapeutic agents are conjugated to hyperbranched polymers (HBPs), such as hyperbranched polyglycerol (HPG). When such conjugates are administered orally to a subject, the HBP protects the therapeutic agent from the acid environment of the stomach and protease attack in the gastrointestinal tract, while facilitating the absorption of the therapeutic agent in the higher pH environment of the intestines. The methods and compositions are useful for the improved administration of a variety of therapeutic agents to a subject.

15 Claims, 23 Drawing Sheets

Scheme 2: Synthesis of carboxylic acid functionalized HPG from HPG

Scheme 3: Conjugation of functionalized HPG to the protein

THERAPEUTIC HYPERBRANCHED POLYGLYCEROL ENCAPSULATED BIOMOLECULES

CROSS-REFERENCE TO RELATED APPLICATION

This application represents the national stage entry of PCT International Application No. PCT/US2015/017055 filed Feb. 23, 2015, which claims priority from U.S. Provisional Application No. 61/943,788, filed on Feb. 24, 2014, which are hereby incorporated by reference herein in their entirety.

STATEMENT REGARDING FEDERALLY SPONSORED RESEARCH OR DEVELOPMENT

Not Applicable.

FIELD OF THE INVENTION

Compositions and methods for facilitating the delivery of a therapeutic agent are disclosed. One method for administering the therapeutic agent is by oral or transmucosal delivery. Specifically, the compositions include a hyperbranched polymer (HBP), such as hyperbranched polyglycerol (HPG), conjugated to the therapeutic agent, wherein the hyperbranched polymer protects the therapeutic agent from harsh conditions, such as, protease attack and/or from the acidic environment of the stomach, while facilitating the absorption of the therapeutic agent in the intestines.

BACKGROUND OF THE INVENTION

Therapeutic proteins are the treatment modality of choice for many disorders. Therapeutic proteins have a more clearly defined action mechanism than small molecule drugs. Furthermore, they can be administered using methods that are safer than methods for directly increasing protein expression, such as gene therapy. Advances in biotechnology have accelerated the economical, large-scale production of proteins, vaccines, and hormones, making them readily available for therapeutic applications in medical practices and clinical studies. In recent years, the market penetration of the pharmaceutical protein industry gained substantial momentum. To date over 140 FDA-approved protein drugs have been placed on the market, and more are coming. It would be desirable to be able to deliver such therapeutic proteins and other therapeutic agents through non-invasive oral or transmucosal routes.

As an example, phenylketonuria (PKU), the most common inborn metabolic disorder in the world, affecting 1 of every 1,000 people, is a genetic disorder caused by a mutation in the gene that encodes for the enzyme phenylalanine hydroxylase (PAH). PAH catalyzes the conversion of the amino acid phenylalanine (Phe) to the amino acid tyrosine (Tyr). When a mutation renders this vital enzyme nonfunctional, Phe, which is present in almost every food containing protein, cannot be processed. Phe builds to dangerously high concentrations in the brain and bloodstream in those afflicted with this disease. Left untreated, it causes a wide range of acute cognitive and behavioral defects. These include severe mental retardation, aggression, and seizures.

Delivering phenylalanine ammonia lyase (PAL), a plant enzyme that converts phenylalanine to non-toxic metabolites ammonia and trans-cinnamic acid, is a potential therapy to compensate for the lack of intrinsic PAH. As PKU is a digestion related disease, orally delivering PAL may present an effective noninvasive treatment for PKU that does not require penetration through the gastrointestinal epithelial membrane.

Another example is the possible oral delivery of alcohol degrading enzyme to relieve the pain resulting from alcohol abuse. Alcohol abuse is associated with a variety of organ injuries (such as liver damage), as well as with serious social problems (such as violence and driving under the influence of alcohol (DUI)). Providing a way to quickly eliminate alcohol in-vivo would be a significant step towards solving these problems.

Ethanol-degrading enzymes, which have a well-defined detoxification mechanism and low toxicity, are the most direct and safe antidotes to alcohol abuse. However, the effectiveness of alcohol dehydrogenase is limited by the low extracellular concentration of NAD+. Thus it cannot serve as an effective antidote when the alcohol concentration is high. Furthermore, the associated consumption of NAD+ may cause many undesired metabolic regulations due to alterations of redox status inside a cell, affecting various biological pathways.

In contrast, alcohol oxidase (AOx), which employs molecular oxygen as a substrate, is capable of achieving rapid clearance of alcohol. Thus, delivering AOx orally would be an effective and non-invasive way to detoxify alcohol.

In addition to PAL and AOx, a number of other therapeutic proteins have shown great promise in clinical applications. Together with other protein drugs, such as insulin, calcitonin, interferons, human growth hormone, glucagons, gonadotropin-releasing hormones, encephalin, vaccines, enzymes, hormone analogs, and enzyme inhibitors, these protein therapeutics have a vast market worldwide.

Despite its fast growth in recent years, protein therapy is still in its adolescence. There are a number of reasons for this, including the difficulties associated with delivering functional proteins that retain their catalytic activity, poor protein stability both in vitro and in vivo, and the high degradation and clearance rates associated with protein therapy. These problems are especially significant in the oral administration of therapeutic proteins. Oral administration of drugs is favorable over other routes of administration due to its simplicity and convenience. However, administrating therapeutic proteins orally is problematic, due to the harsh acidic environment in the stomach, the existence of various proteases in relatively high concentrations, and poor oral adsorption of proteins. Strategies to address these issues are ongoing and in high demand in the biotechnology and pharmaceutical industries.

Various strategies have been attempted to improve the oral bioavailability of therapeutic proteins. The main approaches presently include 1) using absorption enhancers to improve the lipophilicity of the protein to favor transmucosal delivery, 2) using protease inhibitors to tune down enzymatic digestion of the protein, and 3) utilizing mucoadhesive polymeric systems to increase the resident time of the protein in GI tract. To date, various oral delivery systems for proteins have been actively developed, especially by pharmaceutical companies in the hopes of rendering various therapeutic proteins clinically useful. Although these attempts have in some cases achieved enhanced protein stability and/or improved transmucosal protein delivery, none of them have been proven to be good enough for clinical applications.

In the case of PKU treatment, investigators in the United Kingdom found that administrating PAL in enteric-coated capsules could reduce blood phenylalanine levels by 25%. Additionally, a Canadian group has been trying to encapsulate PAL in semipermeable microcapsules and to deliver the resulting microcapsules enterically. Ideally, the enterically placed PAL would metabolize dietary phenylalanine before it is absorbed, and phenylalanine in the blood could recirculate into the intestinal lumen to be degraded by the PAL. The enteric delivery of these microcapsules achieved a 50% reduction in the blood phenyalanine concentration in PAHenu2 mice. Although the degree of reduction achieved by this method is insufficient for the adequate treatment of PKU, these results validated the safety and therapeutic potential of enterically delivered PAL.

Further, although alcohol oxidase (AOx) has great potential as an alcohol detoxification agent, it is not well studied in the context of pharmaceutical applications. In the 1980s, it was shown that by injecting alcohol oxidase post alcohol intoxication, blood alcohol concentration could be reduced by up to three fold. However, the large dosage required, high cost, and resulting immune response blocked the further development of AOx-related drugs. As a consequence, little work has been done on the development of AOx-based alcohol detoxification agents, including the oral delivery of AOx.

Accordingly, there is a need in the art for methods and compositions that can be used to effectively overcome the problems associated with the oral delivery of therapeutic agents, such as, functional therapeutic proteins. Specifically, such compositions and methods should enable retention of catalytic activity, protect the therapeutic agent from acid attack and protease degradation, facilitate the absorption of the therapeutic agent, and be non-toxic and biocompatible.

SUMMARY OF THE INVENTION

The inventors demonstrate herein that hyperbranched polymers (HBPs), when conjugated to a therapeutic agent, provide protection to the therapeutic agent. In one embodiment, HBPs of the present invention may be used to protect the therapeutic agent under harsh conditions. The exemplary harsh conditions may include both the harsh acid environment of the stomach and attack by proteases throughout the gastrointestinal tract. In one embodiment, one may still maintain a readily absorbable form of the therapeutic agent in the intestines when HBPs of the present invention are used.

Accordingly, in one aspect, the disclosure encompasses a conjugate for the oral, rectal or transmucosal delivery of a therapeutic agent to a subject. The conjugate includes a therapeutic agent and a hyperbranched polymer conjugated to the therapeutic agent. In certain embodiments, the hyperbranched polymer is hyperbranched polyglycerol (HPG). A non-limiting example of a polyglycerol that can be used to make the conjugate is the polyglycerol having the chemical structure:

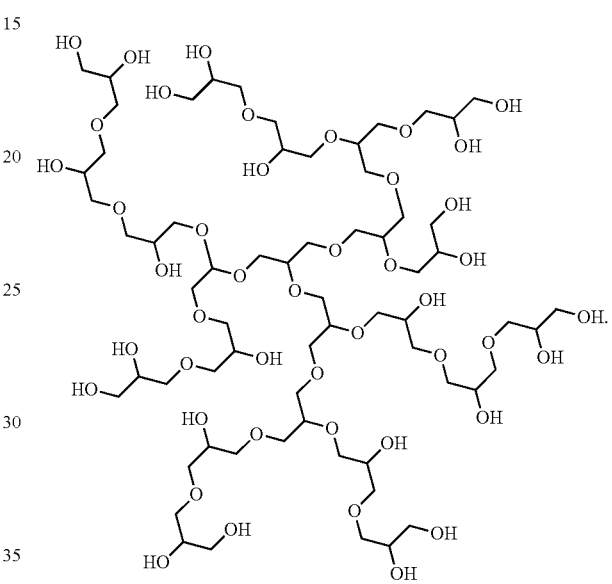

Other exemplary polymers that could be used are shown in the FIGS. 9A-9M.

In certain embodiments, the therapeutic agent is a therapeutic protein. Non-limiting examples of therapeutic proteins that could be used include alcohol oxidase (AOx), phenylalanine ammonia lyase (PAL), insulin, calcitonin, an interferon, human growth hormone, a glucagon, gonadotrophin releasing hormone, encephalin, a vaccine, an enzyme, a hormone analog, an enzyme inhibitor, uricase, lactase, amylase, lipase, a protease, adenosine deaminase, L-asparaginase, and organophosphorous hydrolase. In some such embodiments, the protein is PAL or AOx.

The therapeutic agent and the hyperbranched polymer (HBP) may be conjugated by binding the therapeutic agent to the hyperbranched polymer through one or more functional group(s) on the hyperbranched polymer, by use of a linker moiety, or by binding the therapeutic agent directly to the hyperbranched polymer.

In one embodiment, non-limiting examples of functional groups through which the therapeutic agent may be bound to the hyperbranched polymer may include a ketone, an aldehyde, an imide, a cyano, a haloalkyl, a maleimide derivative, a carboxyl, an activated carboxyl, an activated sulfonyl, sulhydryl, an azide, an isocyanate, an isothiocyanate, a nitrophenylester, and an N-hydroxysuccinimidyl ester. In certain embodiments, the functional group is a carboxyl group. In some such embodiments, the carboxyl group is installed at one or more hydroxyl or amine moieties of the hyperbranched polymer. Optionally, such carboxyl group installation may be performed by contacting the hydroxyl or amine moieties with a cyclic anhydride, such as succinic anhydride.

In certain embodiments wherein the functional group is a carboxyl group, the therapeutic agent and hyperbranched polymer may be conjugated by contacting the carboxyl group with N-hydroxysuccinimide (NHS). As a result of such contact, the carboxyl group is converted to an amine reactive N-hydroxysuccinimidyl carboxylate ester having the formula

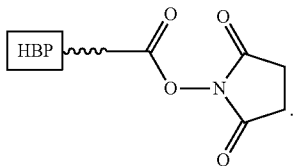

This amine reactive hydroxysuccinimidyl carboxylate ester conjugates with one or more amine moieties on the therapeutic agent to form an amide linkage.

In certain embodiments, the conjugate is in the form of nanoscale particles of a size suitable for transmucosal delivery.

In certain embodiments, the conjugate is in the form of nanoscale particles that aggregate in an acidic environment and that remain dispersed in a neutral or basic environment.

In a second aspect, the disclosure encompasses a pharmaceutical composition that includes the conjugate as described previously and a pharmaceutically acceptable carrier.

In a third aspect, the disclosure encompasses a method of administering a therapeutic agent to a subject. The method includes the steps of conjugating the therapeutic agent to a hyperbranched polymer, and orally, rectally or transmucosally administering the resulting conjugate to the subject.

In certain embodiments, the hyperbranched polymer is hyperbranched polyglycerol (HPG). A non-limiting example of a hyperbranched polyglycerol (HPG) that could be used in the method is the polyglycerol having the chemical structure:

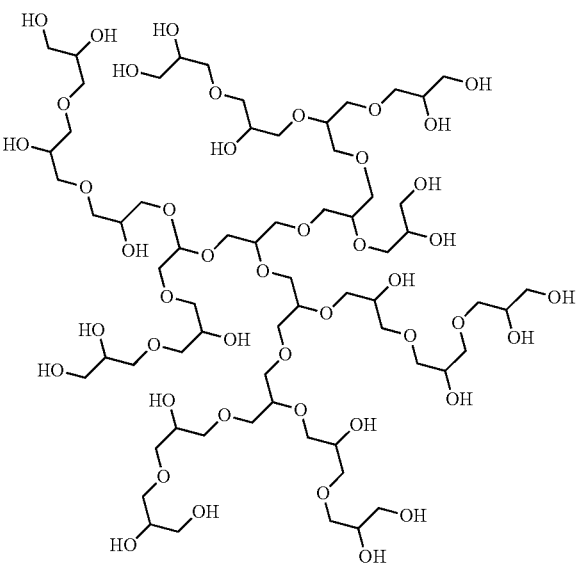 [SMILES: OCC(O)COCC(O)COCC(O)COC(COCC(COCC(O)COCC(O)CO)OCC(O)COCC(O)CO)COC(COCC(COCC(COCC(O)CO)OCC(O)COCC(O)CO)OCC(O)CO)COC(COCC(O)COCC(O)CO)OCC(O)COCC(O)COCC(O)CO]

Other exemplary polymers that could be used are shown in the figures. In one embodiment, HPG of the present invention is selected from the group consisting of exemplary polymers in FIG. 9 (FIGS. 9A-9M).

In certain embodiments, the therapeutic agent is a therapeutic protein. Non-limiting examples of therapeutic proteins that could be used include alcohol oxidase (AOx), phenylalanine ammonia lyase (PAL), insulin, calcitonin, an interferon, human growth hormone, a glucagon, gonadotrophin releasing hormone, encephalin, a vaccine, an enzyme, a hormone analog, an enzyme inhibitor, uricase, lactase, amylase, lipase, a protease, adenosine deaminase, L-asparaginase, and organophosphorous hydrolase. In some such embodiments, the therapeutic protein is PAL or AOx.

The therapeutic agent may be conjugated to the HBP by binding the therapeutic agent to the hyperbranched polymer through one or more functional group(s) on the HBP, through use of a linker moiety, or by binding the therapeutic agent directly to the HBP. In one embodiment, functional groups through which the therapeutic agent may be bound to the HBP include a ketone, an aldehyde, an imide, a cyano, a haloalkyl, a maleimide derivative, a carboxyl, an activated carboxyl, an activated sulfonyl, sulhydryl, an azide, an isocyanate, an isothiocyanate, a nitrophenylester, and an N-hydroxysuccinimidyl ester. In some such embodiments, the functional group is a carboxyl group. When the functional group is a carboxyl group, the step of conjugating the therapeutic agent to the hyperbranched polymer may optionally include the step of installing a carboxyl group at one or more hydroxyl or amine moieties of the hyperbranched polymer. This step can be performed by, for example, contacting the hydroxyl or amine moieties with a cyclic anhydride, such as succinic anhydride.

Optionally, when the functional group is a carboxyl group, the step of conjugating the therapeutic agent to the hyperbranched polymer may include the step of contacting the carboxyl group with N-hydroxysuccinimide (NHS). The carboxyl group is then converted to an amine reactive N-hydroxysuccinimidyl carboxylate ester having the formula:

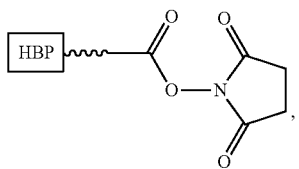

and the amine reactive hydroxysuccinimidyl (NHS) carboxylate ester is conjugated with one or more amine moieties on the therapeutic agent to form an amide linkage.

In certain embodiments, the conjugate is delivered to the subject orally. In some such embodiments, the conjugate may be in the form of nanoscale particles that aggregate in an acidic environment and that remain dispersed in a neutral or basic environment.

In a fourth aspect, the disclosure encompasses a method for making a conjugate for the oral or transmucosal delivery of a therapeutic agent to a subject. The method includes the step of conjugating a therapeutic agent to a hyperbranched polymer, whereby a conjugate is formed.

In certain embodiments, the hyperbranched polymer is hyperbranched polyglycerol (HPG). A non-limiting example of a hyperbranched polyglycerol (HPG) that could be used is the polyglycerol having the chemical structure:

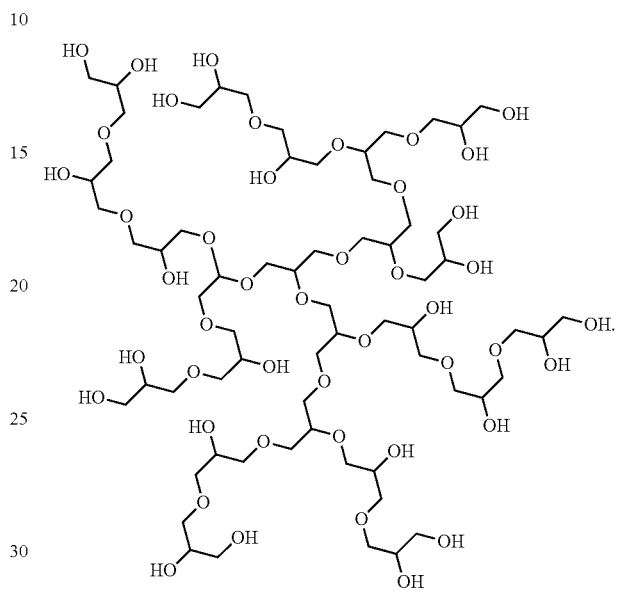

Other exemplary polymers that could be used are shown in the figures. In one embodiment, HPG of the present invention is selected from the group consisting of exemplary polymers in FIG. 9 (FIGS. 9A-9M).

Specifically, a HPG that could be used is the polyglycerol having the chemical structure selected from the group consisting of

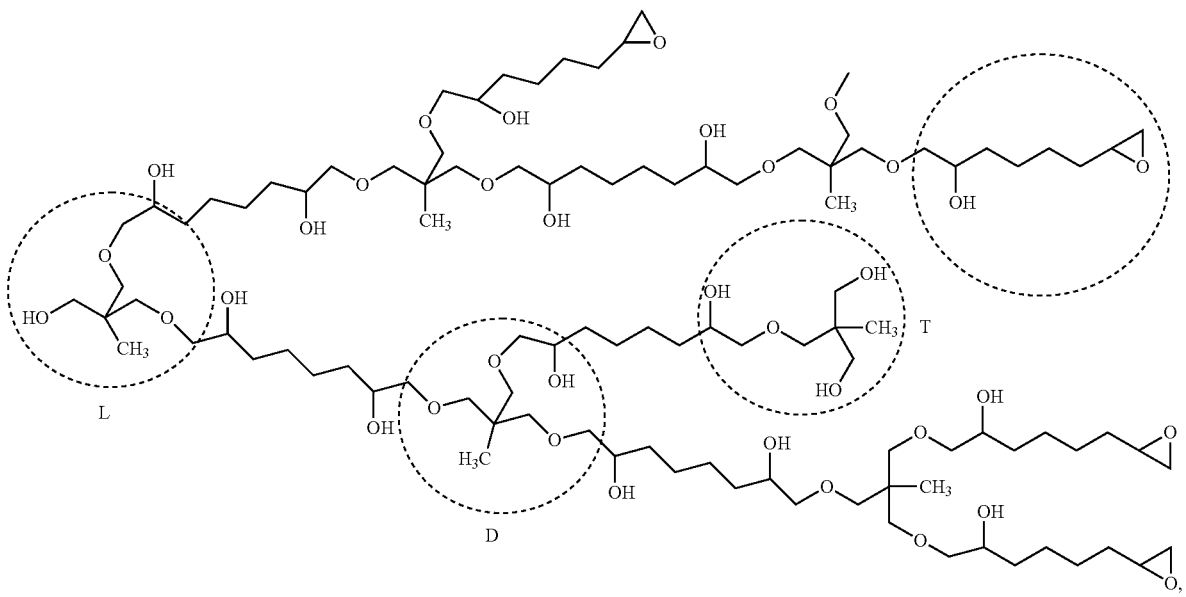

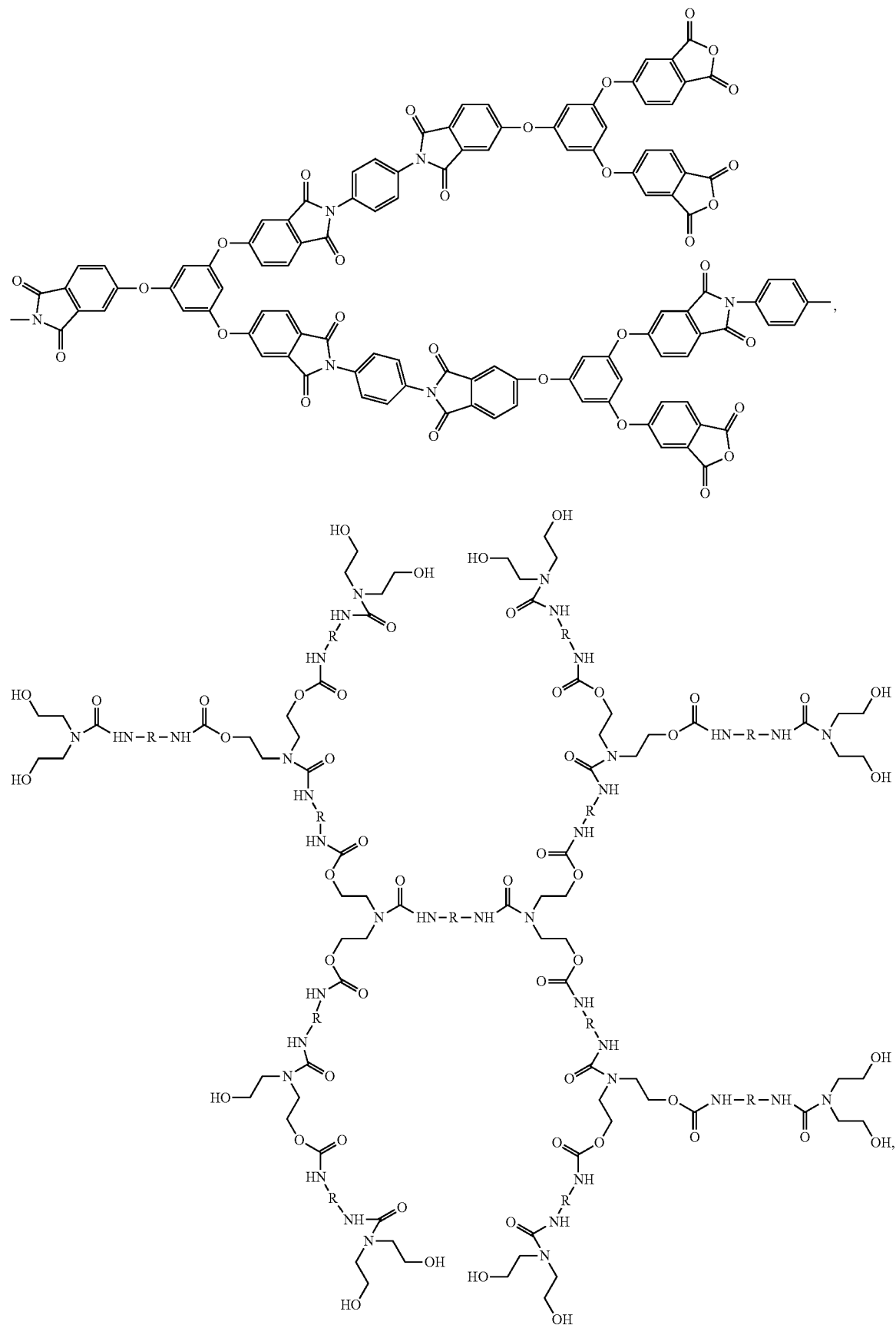

-continued
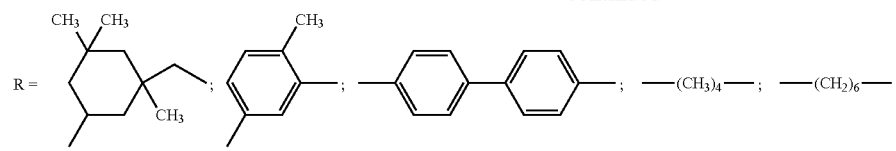
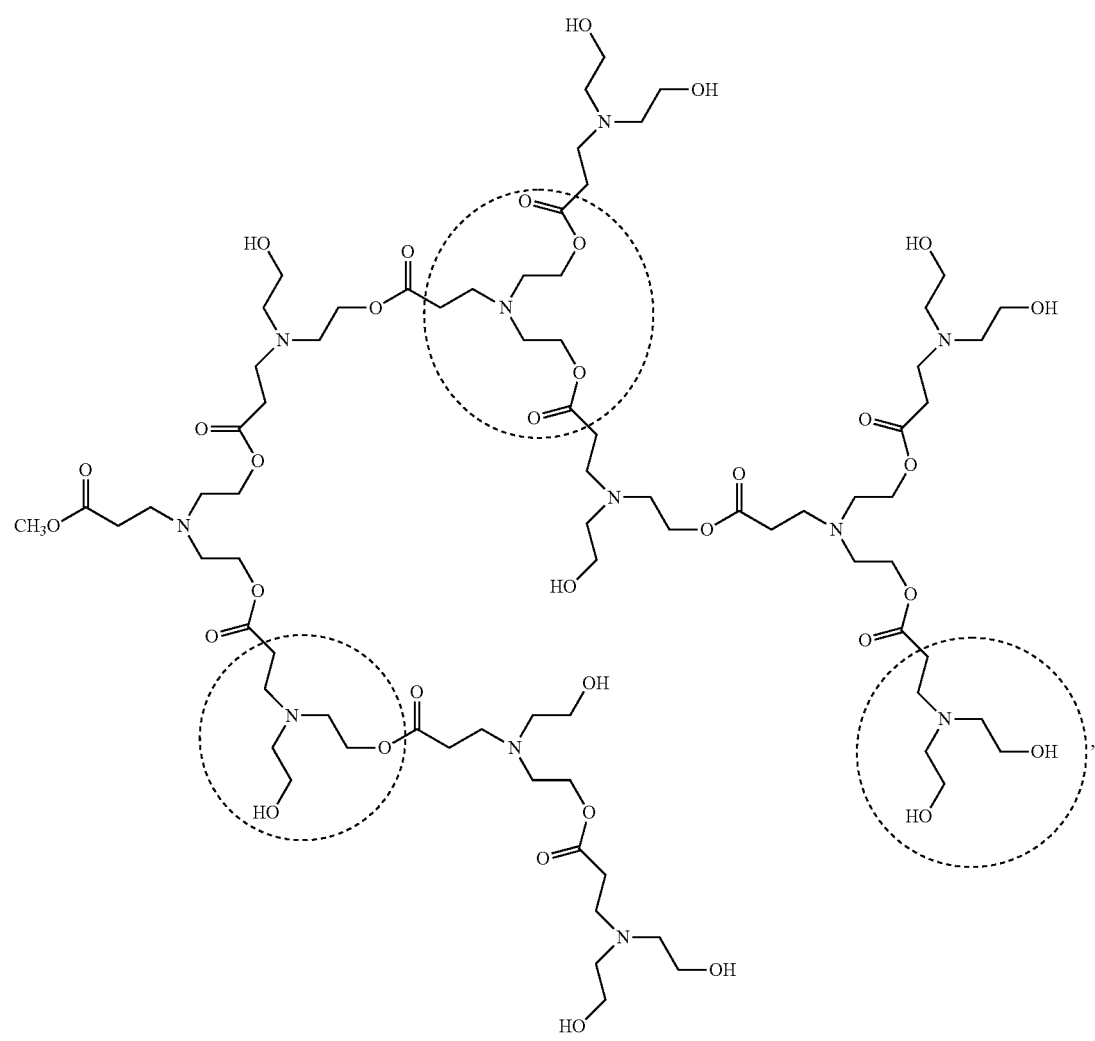

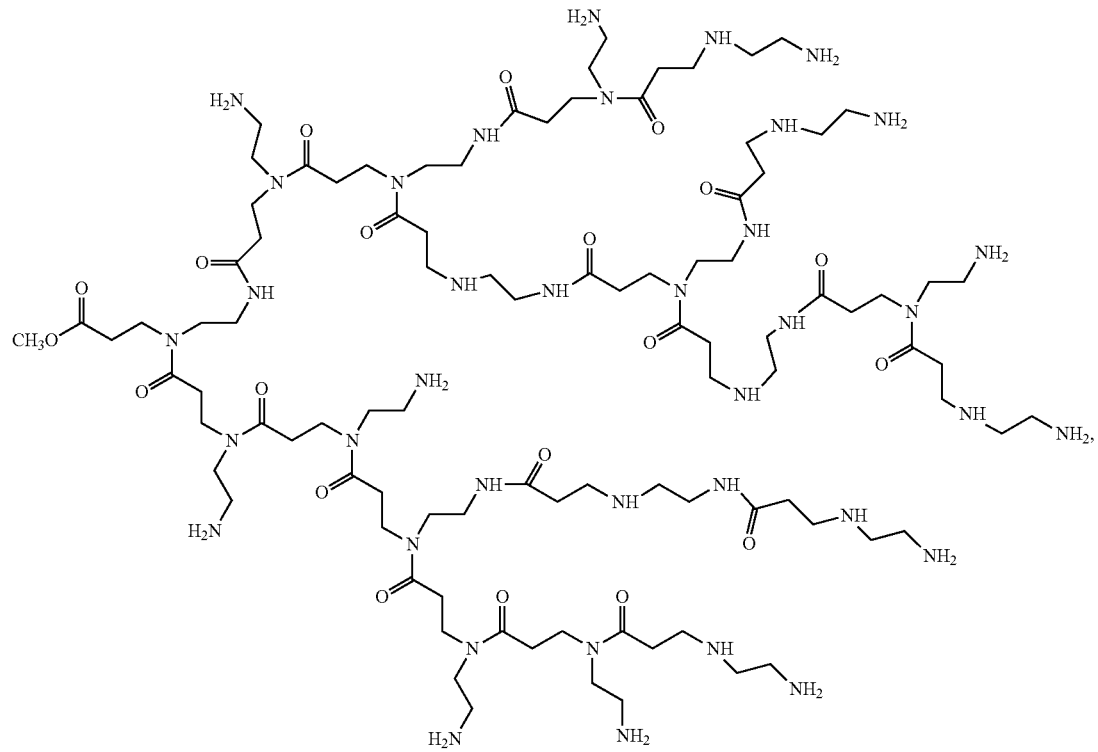
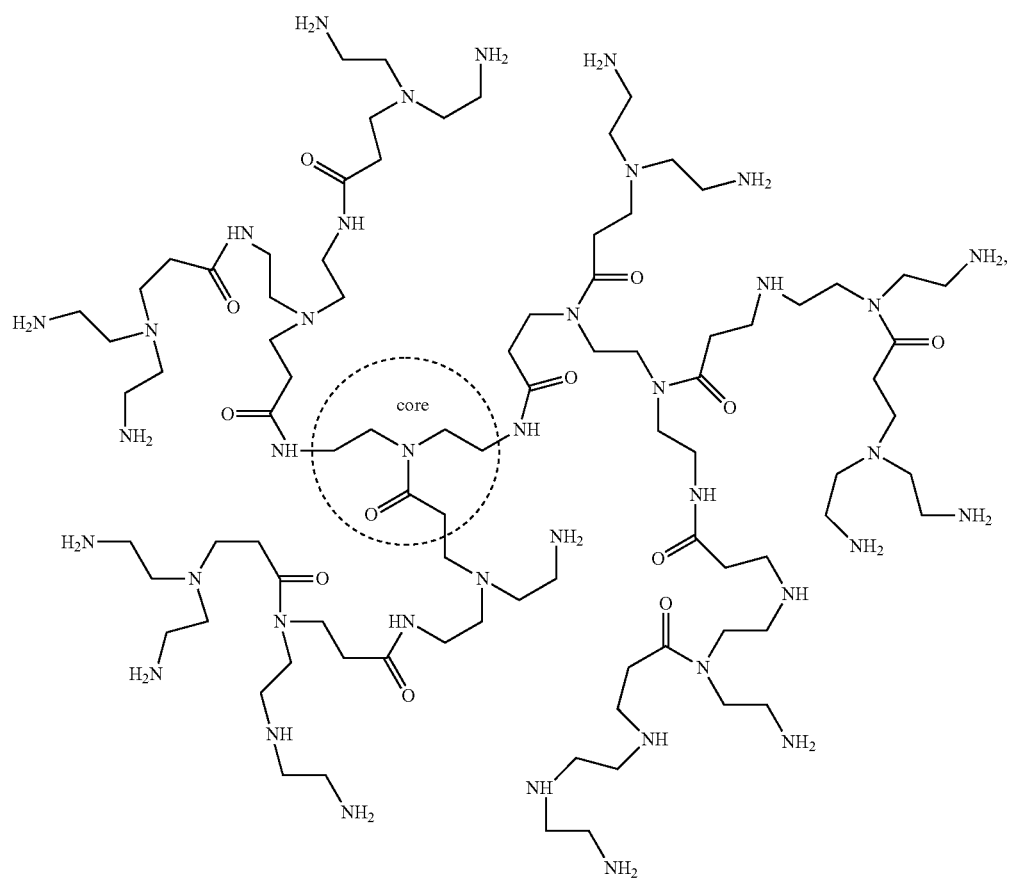

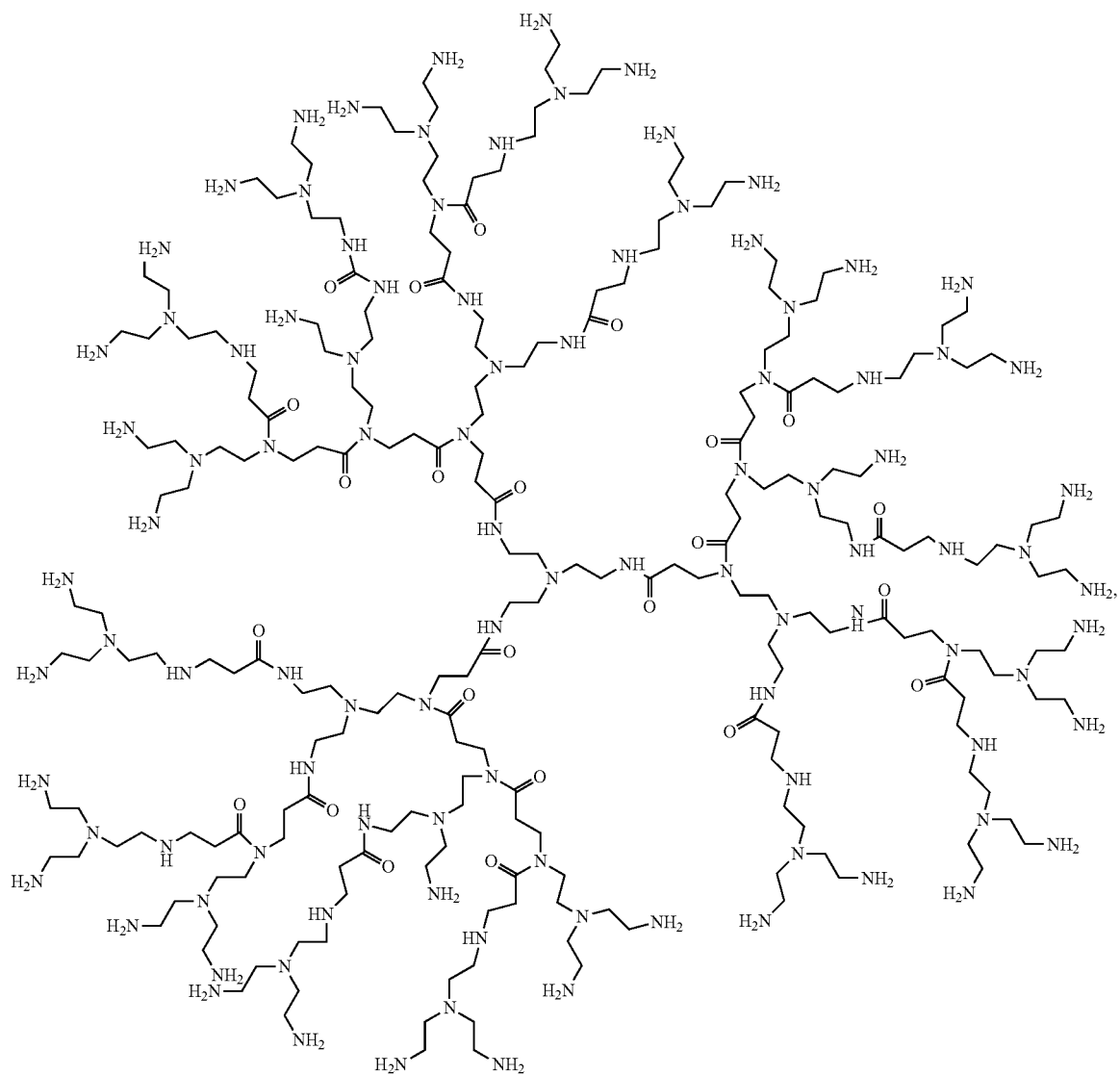 [SMILES: NCCN(CCN)CCNCCC(=O)NCCN(CCNC(=O)CCN(CCN(CCN)CCN)C(=O)CCNCCN(CCN)CCN)CCN(CCC(=O)NCCN(CCNC(=O)CCN(CCN(CCNC(=O)CCNCCN(CCN)CCN)CCNC(=O)CCN(CCN(CCN)CCN)C(=O)CCNCCN(CCN)CCN)C(=O)CCN(CCN(CCN)CCNC(=O)CCNCCN(CCN)CCN)C(=O)CCN(CCN(CCN)CCN)C(=O)CCNCCN(CCN)CCN)CCNC(=O)CCN(CCN(CCNC(=O)CCNCCN(CCN)CCN)CCNC(=O)CCN(CCN(CCN)CCN)C(=O)CCNCCN(CCN)CCN)C(=O)CCN(CCN(CCN)CCNC(=O)NCCN(CCN)CCN)C(=O)CCN(CCN(CCN)CCN)C(=O)CCNCCN(CCN)CCN)C(=O)CCN(CCN(CCN)CCNC(=O)CCNCCN(CCN)CCN)C(=O)CCN(CCN(CCN)CCN)C(=O)CCNCCN(CCN)CCN]

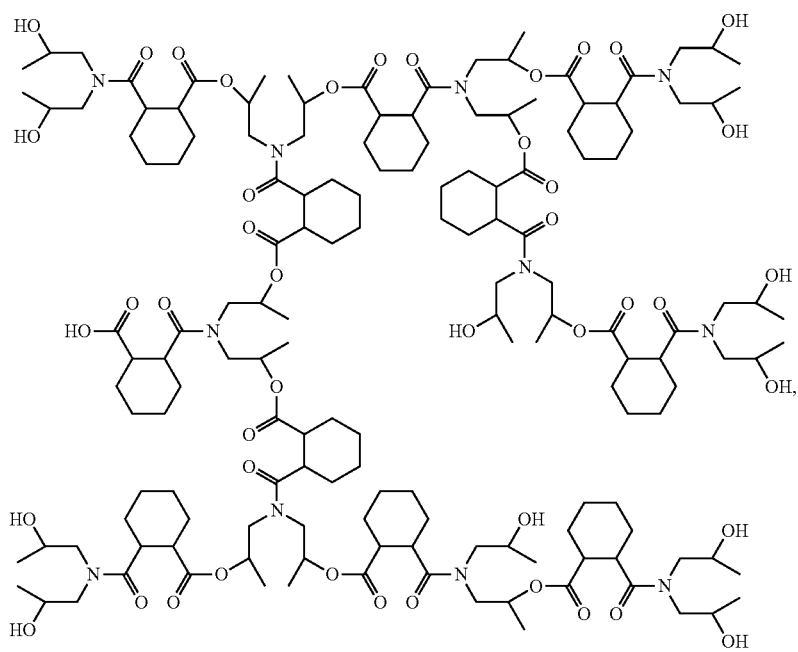
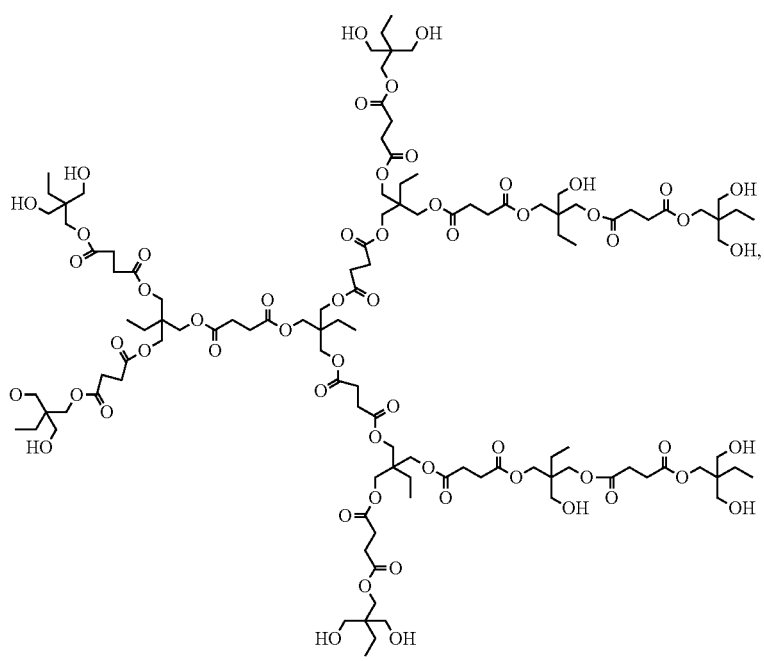

-continued
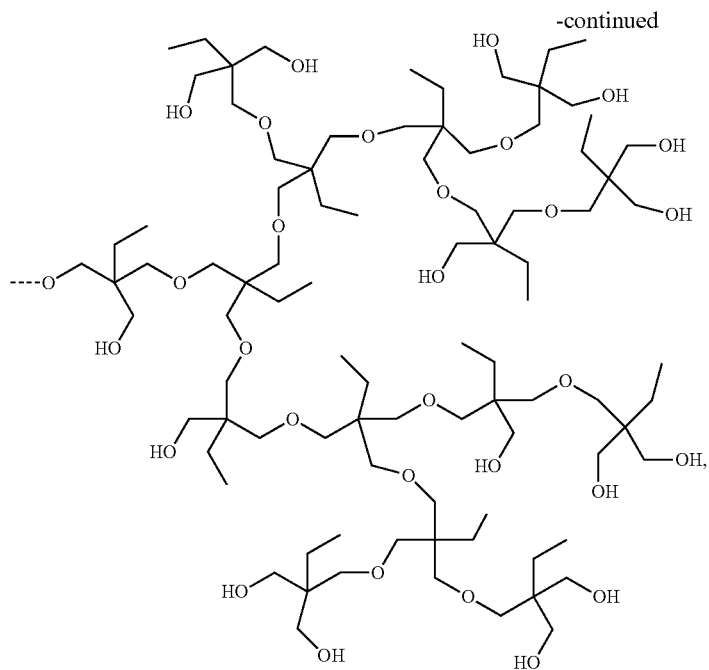
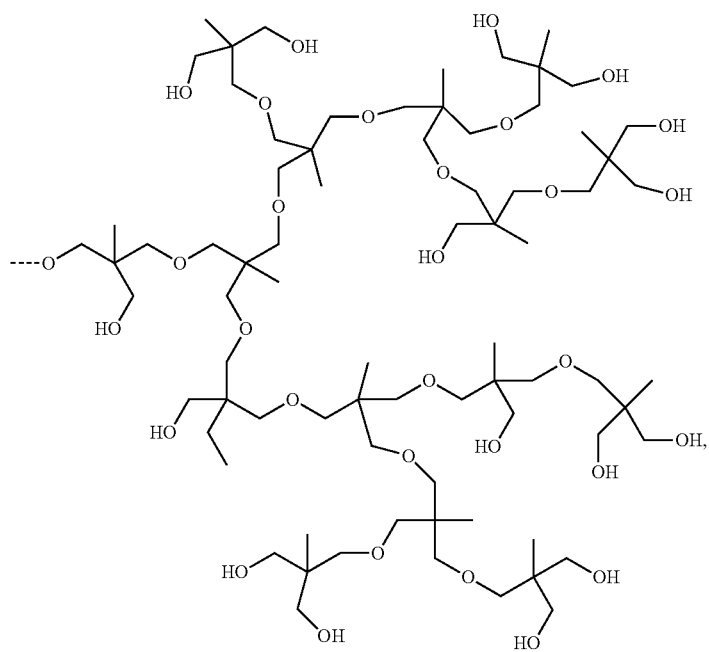

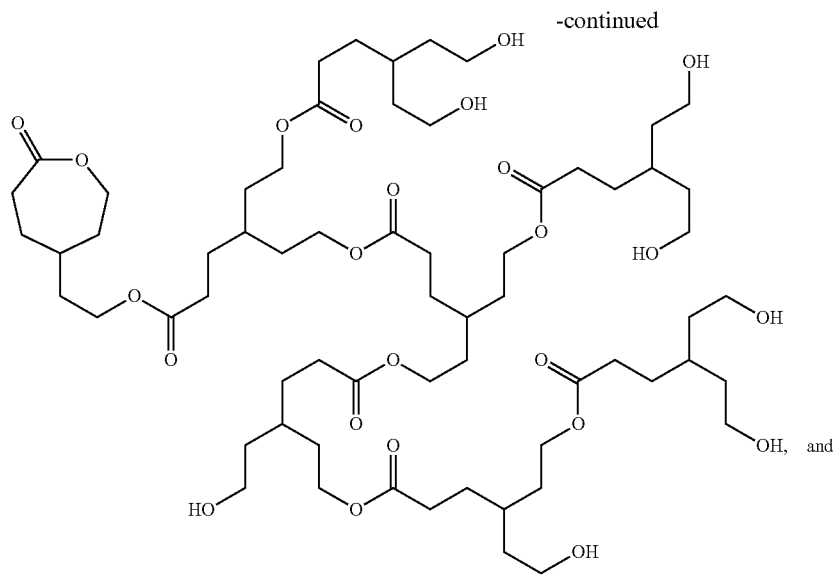

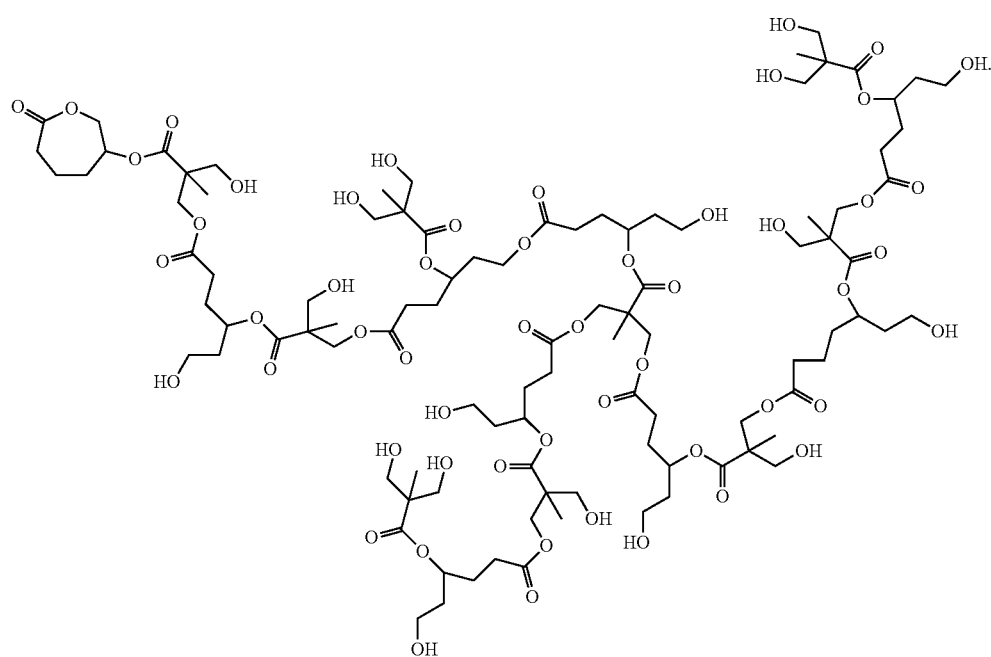

In certain embodiments, the therapeutic agent is a therapeutic protein. Non-limiting examples of therapeutic proteins that could be used include alcohol oxidase (AOx), phenylalanine ammonia lyase (PAL), insulin, calcitonin, an interferon, human growth hormone, a glucagon, gonadotrophin releasing hormone, encephalin, a vaccine, an enzyme, a hormone analog, an enzyme inhibitor, uricase, lactase, amylase, lipase, a protease, adenosine deaminase, L-asparaginase, and organophosphorous hydrolase. In some such embodiments, the therapeutic protein is PAL or AOx.

Optionally, the hyperbranched polymer may include or be modified to include a carboxyl functional group. In such embodiments, the step of conjugating the therapeutic agent to the hyperbranched polymer may include the step of reacting the carboxyl functional group with an amino moiety on the therapeutic agent to form an amide linkage, thereby conjugating the hyperbranched polymer to the therapeutic agent. In some such embodiments, the hyperbranched polymer includes one or more hydroxyl or amine moieties, and the method further includes the step of modifying the one or more hydroxyl or amine moieties to install a carboxyl functional group by contacting the hydroxyl or amine moieties with a cyclic anhydride, such as succinic anhydride.

Optionally, the step of conjugating the therapeutic agent to a hyperbranched polymer including a carboxyl group further comprises the step of contacting the carboxyl group with N-hydroxysuccinimide (NHS), whereby the carboxyl group is converted to an amine reactive N-hydroxysuccinimidyl carboxylate ester having the formula

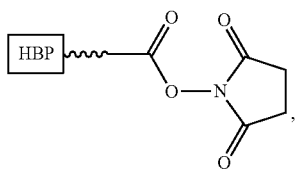

wherein the amine reactive hydroxysuccinimidyl carboxylate ester is conjugated with one or more amine moieties on the therapeutic agent to form an amide linkage.

These and other features of the present invention will become apparent to the skilled artisan from the following detailed description and incorporated Appendix materials considered in conjunction with the accompanying drawings.

DETAILED DESCRIPTION OF THE INVENTION

In General

Figure 1:
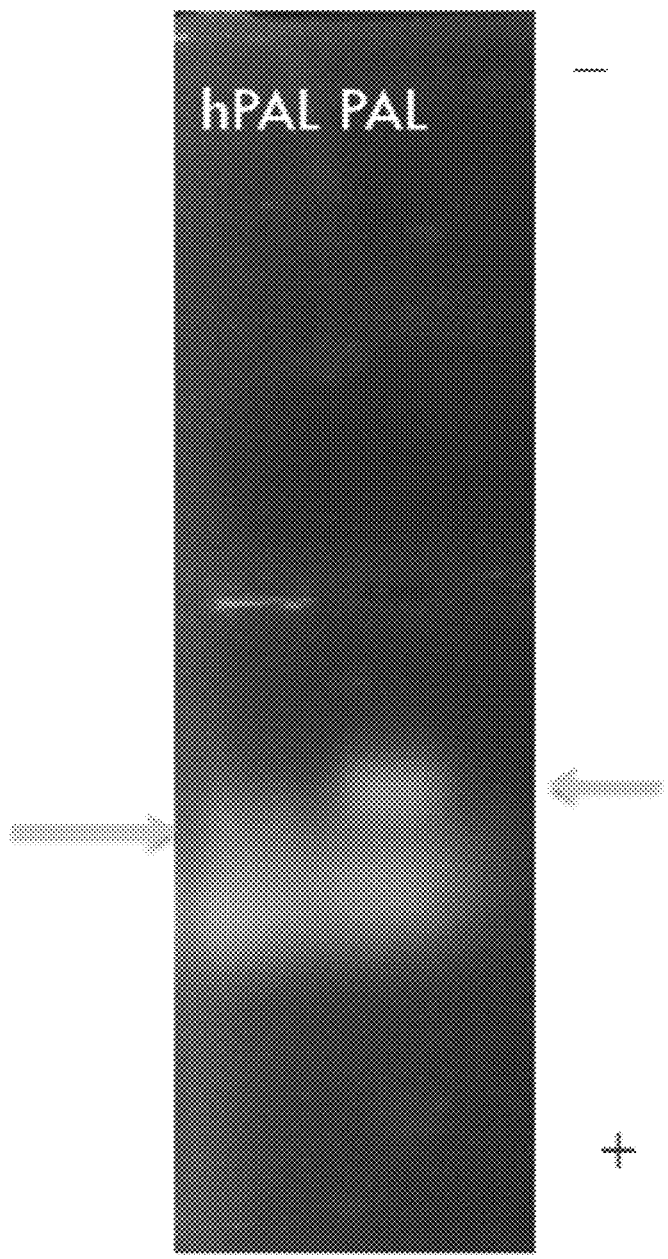
FIG. 1 is an electrophoresis gel image distinguishing between native PAL (right lane) and PAL that is successfully conjugated with hyperbranched polyglycerol (HPG; left lane).

Before the present compositions and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference in their entirety for all purposes including describing and disclosing the chemicals, instruments, statistical analysis and methodologies which are reported in the publications which might be used in connection with the invention. All references cited in this specification are to be taken as indicative of the level of skill in the art Nothing herein is to be construed as an admission that the invention is not entitled to antedate such disclosure by virtue of prior invention.

The Invention

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed nonprovisional applications.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

As a means of simplifying the discussion and the recitation of certain terminology used throughout this application, the terms "group" and "moiety" are used to differentiate between chemical species that allow for substitution or that may be substituted and those that, in the particular embodiment of the invention, do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The terms "hydroxy" and "hydroxyl" refer to the group —OH.

The term "carboxylate" or "carboxyl" refers to the group —COO$^-$ or —COOH.

The term "cyano" refers to the group —CN.

The term "amino" refers to the group —NH$_2$.

The term "acyl" or "aldehyde" refers to the group —C(═O)H.

The term "ketone" refers to the group —C(═O)R$_1$R$_2$ (R$_1$≠H and R$_2$≠H).

The term "sulfhydryl" refers to the group R—SH.

The term "thiocyano" refers to the group —S—CN.

The term "2,4-pentanedione" refers to the compound CH$_3$—C(O)—CH$_2$—C(O)—CH$_3$.

The term "hydrazido" refers to the group "—C(O)—NH—NH$_2$

The term "amido" or "amide" refers to the group —C(O)NH$_2$.

The term "aminooxy" refers to the group —ONH$_2$.

The term "aminoacyl" or "acylamino" refers to the group —NHC(O)H.

The term "thiol" refers to the group —SH.

The term "thioxo" refers to the group ═S.

The term "sulfinyl" refers to the group —S(═O)H.

The term "sulfonyl" refers to the group —SO$_2$H.

The term "sulfonylamido" or "sulfonamide" refers to the group —SO$_2$NH$_2$.

The term "sulfonate" refers to the group SO$_3$H and includes groups having the hydrogen replaced with, for example a C$_{1-6}$alkyl group ("alkylsulfonate"), an aryl ("arylsulfonate"), an aralkyl ("aralkylsulfonate") and so on. C$_{1-3}$sulfonates are preferred, such as for example, SO$_3$Me, SO$_3$Et and SO$_3$Pr.

The term "isomers," as used herein, refer to stereoisomers, diastereomers, enantiomers and tautomers. "Tautomers" may be isomers that are readily interconvertable by rapid equilibrium. For example, carbonyl compounds that have a hydrogen on their alpha-carbon are rapidly interconverted with their corresponding enols.

As used herein, the terms "alkyl," "alkenyl," and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "heterocyclic" includes cycloalkyl or cycloalkenyl non-aromatic rings or ring systems that contain at least one ring heteroatom (e.g., O, S, N).

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are difluoromethyl, trifluoromethyl, and the like. "Halogens" are elements including chlorine, bromine, fluorine, and iodine.

The term "aryl" as used herein includes monocyclic or polycyclic aromatic hydrocarbons or ring systems. Examples of aryl groups include phenyl, naphthyl, biphenyl, fluorenyl and indenyl. Aryl groups may be substituted or unsubstituted. Aryl groups include aromatic annulenes, fused aryl groups, and heteroaryl groups. Aryl groups are also referred to herein as aryl rings.

The term "phenylalanine ammonia lyase" or "PAL," as used herein, refers to an enzyme that catalyzes a reaction converting L-phenylalanine to ammonia and trans-cinnamic acid. Phenylalanine ammonia lyase (PAL) is the first and committed step in the phenyl propanoid pathway and is therefore involved in the biosynthesis of the polyphenol compounds such as flavonoids, phenylpropanoids, and lignin in plants. Phenylalanine ammonia lyase is found widely in plants, as well as some yeast and fungi, with isoenzymes existing within many different species. It has a molecular mass in the range of 270-330 kDa. The activity of PAL is induced dramatically in response to various stimuli such as tissue wounding, pathogenic attack, light, low temperatures, and hormones. PAL has recently been studied for possible therapeutic benefits in humans afflicted with phenylketonuria. It has also been used in the generation of L-phenylalanine as precursor of the sweetener aspartame.

The term "conjugate" or "conjugation," as used herein, refer to connecting two molecules by chemical bonds or any other means of attraction for the purpose of protecting the molecules. The means of attraction may include, but not limited to, dipole-dipole interactions, the London dispersion force, hydrogen bonding and electrostatic interaction. In one embodiment, HBPs are conjugated with a therapeutic agent to protect the therapeutic agent. In some embodiments, the term "conjugate" may also refer to a complex comprising HBPs connecting to therapeutic agents. The term "nanoconjugate" refers to a conjugate of HBPs with therapeutic agents which has an average size of 0.1 nm-10 μm, preferably 1 nm-1 μm, more preferably 1 nm-900 nm.

The term "therapeutically effective amount" of a medicament, composition or compound, as used herein, refers to an amount of the medicament, composition or compound in such a concentration to result in a therapeutic level of drug delivered over the term that the drug is used. This may be dependent on mode of delivery, time period of the dosage, age, weight, general health, sex and diet of the subject receiving the medicament, composition or compound.

The term "cross-linked," as used herein refers to both partial and complete cross-linking of polymer chains by a grouping that bridges or links two chains.

The term "homopolymer," as used herein refers to a polymer formed from a single monomer.

The term "heteropolymer," as used herein refers to a polymer formed from more than a single monomer.

As used herein, the term "functional group(s)" refers to a group that includes one or a plurality of atoms other than hydrogen and $sp^3$ carbon atoms. Examples of functional groups include but are not limited to hydroxyl (—OH), protected hydroxyl, ether (—C—O—C—), ketone (>C=O), ester (—C(=O)O—C—), carboxylic acid (—C(=O)OH), cyano (—C≡N), amido (—C(=O)NH—C—), isocyanate (—N=CO), urethane (—O—C(=O)—NH—), urea (—NH—C(=O)—NH—), protected amino, thiol (—SH), sulfone, sulfoxide, phosphine, phosphite, phosphate, halide (—X), and the like. In one embodiment, the functional group may include a ketone, an aldehyde, an imide, a cyano, a haloalkyl, a maleimide derivative, a carboxyl, an activated carboxyl, an activated sulfonyl, sulhydryl, an azide, an isocyanate, an isothiocyanate, a nitrophenylester, and an N-hydroxysuccinimidyl ester.

The term "subject," as used herein, refers to a human patient or any other test subject, e.g., a primate, or other mammal, such as a rat, mouse, dog, cat, cow, pig, sheep or the like.

The term "administering" or "administration," as used herein, refers to providing the compound or pharmaceutical composition of the invention to a subject suffering from or at risk of the diseases or conditions to be treated or prevented.

The term "systemic delivery," as used herein, refers to any suitable administration methods which may delivery the compounds in the present invention systemically. In one embodiment, systemic delivery may be selected from the group consisting of oral, parenteral, intranasal, inhaler, sublingual, rectal, transmucosal, and transdermal administrations. In one specific embodiment, systemic delivery may be selected from the group consisting of oral, rectal and transmucosal delivery.

A route of administration in pharmacology and toxicology is the path by which a drug, fluid, poison, or other substance is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

The examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

The examples for parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

In one preferred embodiment, the present invention provides a conjugate protecting a therapeutic agent during administration through the gastrointestinal tract, sometimes termed enteral or enteric administration. Enteral/enteric administration usually includes oral (through the mouth) and rectal (into the rectum) administration, in the sense that these are taken up by the intestines. In one embodiment, the preferred administration also includes transmucosal administration.

The term "hyperbranched polymer" or "HBP," as used herein, refers to polymers that incorporate plural copies of at least one branching monomer unit. For example, many polymers are comprised of monomer units that only have two reacting groups. Accordingly, the polymers prepared from such monomers are linear. In contrast, hyperbranched polymers (HBPs) incorporate monomers that have three or more reacting groups and thus result in branched polymers. HBPs may be homopolymers, composed of monomers that all have the potential for branching sites, or can be copolymers of branching monomers (those able to react three or more times) with other branching monomers or with linear monomers (those able to react only two times). (see, e.g., Gao and Yan, *Prog. Polym. Sci.* 29 (2004) 183-275 incorporated by reference in its entirety for all purposes).

The HBP compounds employed herein typically are considered to be biocompatible or pharmaceutically acceptable polymers, such that they are suitable for administration to human and/or veterinary subjects. Certain disclosed embodiments of the HBP, e.g., the hyperbranched polyglycerol (HPG) polymer are homopolymers that contain only repeating glycerol subunits. In another example, the HPG polymer may be a heteropolymer that includes one, two or more other polymer subunits.

HBPs are well known in the art (see, e.g., Gao and Yan, *Prog. Polym. Sci.* 29 (2004) 183-275). Examples of HPG polymer compounds, methods of synthesizing them using, for example, a single monomer methodology and double-monomer methodology, modifying, and functionalizing the compounds are disclosed herein and in *Macromolecules* 1999, 32, 4240-4246 (polyglycerol) and Biomaterials 2006, 27:5471-5479, and Gao and Yan, *Prog. Polym. Sci.* 29 (2004) 183-275, all of which references are incorporated herein by reference their entirety.

The HBPs that may be used in the disclosed compositions and methods also include dendrimers. Dendrimers are highly branched polymers and oligomers having a well-defined chemical structure. Dendrimers include a core, a given number of generations of branches, or arms, and end groups. The generations of arms consist of structural units that are identical for the same generation of arms and which may be identical or different for different generations of arm. The generations of arms extend radially in a geometrical progression from a core. The end groups of a dendrimer from the Nth generation are the end functional groups of the arms of the Nth generation or end generation. Dendrimers may includes molecules containing symmetrical branching; they may also include molecules containing non-symmetrical branching. Dense star polymers, starburst polymers and rod-shaped dendrimers may be included in the dendrimers described herein. Several hyperbranched compounds or dendrimers may also be combined together, via a covalent bond or another type of bonding, by means of their end groups to give bridged species.

In one embodiment, the HBPs that may be used in the disclosed compositions and methods may also include metallodendrimers. As used herein, the term "metallodendrimer" refers to a type of dendrimer with incorporated metal atoms. In one embodiment, the metal can be situated in the repeat unit, the core or at the extremities as end-group. Elements often encountered may be palladium and platinum. These metals can form octahedral six-coordinate M(IV) linking units from organic dihalides and the corresponding 4-coordinate M(II) monomers. Ferrocene-containing dendrimers and dendrimers with cobaltocene and arylchromiumtricarbonyl units have been reported in end-functional dendrimers. Metallodendrimers may form as metal complexes with dendritic counter ions for example by hydrolysis of ester terminated PAMAM dendrimers with sodium hydroxide.

In one embodiment, the HBPs that may be used in the disclosed compositions and methods may also include dendronized polymers. As used herein, the term "dendronized polymers" or "dendronised polymers" refers to linear polymers to every repeat unit of which dendrons are attached. Dendrons are regularly branched, tree-like fragments and for larger ones the polymer backbone is wrapped to give sausage-like, cylindrical molecular objects.

The term "hyperbranched polyglycerol" or "HPG," as used in herein, refers to a glycerol polymer having a plurality of branch points and multifunctional branches that lead to further branching with polymer growth. Hyperbranched polymers may be obtained by a one-step polymerization process and form a polydisperse system with varying degrees of branching. Methods of making a variety of such polymers are known in the art (for example PCT/CA2006/000936), and further described herein.

The average molecular weight (Mn) of the hyperbranched polyglycerol polymers of the present invention may be from about 2 K to about 1200K, or any amount therebetween; from 10K to about 750K or any amount therebetween; from about 20K to about 200K or any amount therebetween; from about 30K to about 100K, or any amount therebetween; or from about 35K to about 90K, or any amount therebetween. For example, the average molecular weight of the HPGs may be 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 32 0, 330, 340, 350, 400, 450, 500, 550, 600, 650, 700, 750, 800, 850, 900, 950, 1000, 1050, 1100, 1150 or 1200 K, or any amount there-between.

In one embodiment, Applicants demonstrate herein that HBPs, when conjugated to a therapeutic agent, such as a therapeutic protein, provide protection against harsh conditions while maintaining a readily absorbable form of the therapeutic agent. In one specific embodiment, conjugation of HBPs with a therapeutic agent provides protection against both the harsh acid environment of the stomach and attack by proteases throughout the gastrointestinal tract, while maintaining a readily absorbable form in the intestines. In one embodiment, hyperbranched polymers (HBPs) may be those that comprise high negative charge, such as hyperbranched polyglycerol (HPG).

Accordingly, in one aspect, the disclosure encompasses a conjugate, i.e., a complex of HBPs conjugated to a therapeutic agent, for the oral or transmucosal delivery of the therapeutic agent to a subject. In one embodiment, the conjugate includes a therapeutic agent and at least a HBP conjugated to the therapeutic agent Applicants envision a conjugate of the present invention may also includes a therapeutic agent and two or more HBPs conjugated to the therapeutic agent.

In certain embodiments, the conjugate is a nanoconjugate comprising a HBP, and in some such embodiments, a HPG.

In one embodiment of the present invention, HBP is conjugated to a therapeutic agent. In some embodiments, the therapeutic agent becomes encapsulated by the conjugated HBP. In another embodiment, the conjugated HBP may be any suitable polymer as appreciated by one skilled in the art. In one specific embodiment, the HBP of the present invention is a HPG.

In one embodiment, the HBP of the present invention may include any other suitable hyperbranched polymers with long arms as appreciated by one skilled in the art. For example, FIGS. 9A to 9M depict examples of a few polymers that may be functionalized to encapsulate biomolecules for oral delivery.

The term "therapeutic agent," as used herein, encompasses any agent having biological activity that can be administered to a subject for therapeutic purposes, such as a biomolecule. As used herein, therapeutic agent may be characterized broadly as any ligand moiety, such as antibodies, growth factors, cytokines, cell adhesion molecules, their receptors, peptides, proteins, enzymes or small molecules, such as a receptor agonists, antagonists or enzyme inhibitors.

In certain embodiments, the therapeutic agents are proteins. The term "protein," as used herein, encompasses proteins, peptides, polypeptides, glycopeptides, oligopeptides and any other suitable forms of proteins. It is understood that when a therapeutic agent is a protein, functional or catalytically active fragments, truncations, functional residues and derivatives thereof also are intended.

Proteins may be synthetic or naturally occurring, and may be obtained by chemical synthesis, or by recombinant or non-recombinant methods. The protein may be produced using DNA recombination or mutation techniques. The protein may be produced in vivo in a whole animal, or in a eukaryotic or prokaryotic cell; alternatively, the protein may be generated using an in vitro method such as cell-free in vitro translation e.g. using *E. coli* lysate, wheat germ extract, or rabbit reticulocyte. Cell free in vitro translation methods can be employed following in vitro transcription, e.g. following phage or ribosome display. In certain embodiments, a protein produced using recombinant techniques or in vitro translation system may be purified prior to being used in the compositions and methods of this application. In other embodiments the recombinant protein remains substantially unpurified from other proteins of the host cell or in vitro translation system before being in the composition and methods of this application.

Examples of proteins useful in the method may include, without limitation, Lysozyme, Adenosine deaminase, L-Asparaginase, Mammalian urate oxidase, Interferons, Anti-TNF a Fab, G-CSF, Continuous srythropoietin receptor activator, hGH antagonist B2036, Insulin, Insulin human inhalation, Insulin aspart, insulin glulisine, insulin lispro, Isophane insulin, Insulin detemir, insulin glargine, Insulin zinc extended, Pramlintide acetate, Growth hormone (GH), Somatotropin, Mecasermin, Mecasermin rinfabate, Factor VIII. Factor IX, Antithrombin III (AT-iii), fibroblast growth factor (FGF), basic fibroblast growth factor (bFGF), vascular endothelial growth factor (VEGF), platelet derived growth factor (PDGF), Protein C concentrate, β-Glucocerebrosidase, Alglucosidase-α, Laronidase (α-L-iduronidase), Idursulphase (iduronate-2-sulphatase), Galsulphase, Agalsidase-β (human α-galactosidase A), α-1-Proteinase inhibitor, Lactase, Pancreatic enzymes, lipase, amylase, protease, Adenosine deaminase, Pooled immunoglobulins, Human albumin, Erythropoietin, Epoetin-α, Darbepoetin-α, Sargramostim (granulocytemacrophage colony stimulating factor; GM-CSF), Oprelvekin (interleukin11; IL11) Human follicle-stimulating hormone (FSH), Human chorionic gonadotropin (HCG), Lutropin-α, Type I alpha-interferon, interferon alfacon 1, consensus interferon, Aldesleukin (interleukin 2 (IL2), epidermal thymocyte activating factor (ETAF), Alteolase (tissue plasminogen activator: tPA), Reteplase (deletion mutein of tPA), Tenecteplase, Urokinase, Factor VIIa, Drotrecogin-α (activated protein C), calcitonin, Salmon calcitonin, Teriparatide (human parathyroid hormone residues 1-34), Exenatide, Octreotide, Dibotermin-α (recombinant human bone morphogenic protein 2; rhBMP2), Recombinant human bone morphogenic protein 7 (rhBMP7), Histrelin acetate (gonadotropin releasing hormone; GnrH), Palifermin (keratinocyte growth factor; KGF), Becaplermin (platelet-derived growth factor; PDGF), Trypsin, Nesiritide, Botulinum toxin type A, Botulinum toxin type B, Collage, Collagenase, Human deoxyribonuclease I, dornase-α, Hyaluronidase (bovine, ovine), Hyaluronidase (recombinant human), Papain, L-Asparaginase, Rasburicase, Lepirudin, Bivalirudin, Streptokinase, Anistreplase (anisoylated plasminogen streptokinase activator complex; APSAC), Bevacizumab, Cetuximab, Panitumumab, Alemtuzumab, Rituximab, Trastuzumab, Abatacept Anakinra, Adalimumab, Etanercept, Infliximab; Alefacept, Efalizumab, Natalizumab, Eculizumab, Antithymocyte globulin (rabbit), Basiliximab, Daclizumab, Muromonab-CD3, Omalizumab, Palivizumab, Enfuvirtide, Abciximab, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, and itositumomab.

The therapeutic agents that may be used in the disclosed compositions and methods may include enzymes. The term "enzyme", as used herein, refers to any substance that catalyzes or promotes one or more chemical or biochemical reactions, which usually includes enzymes totally or partially composed of a polypeptide. But the term "enzyme" may also include enzymes composed of a different molecule, e.g., polynucleotides. The enzymes may be wild-type enzymes or variant (genetically engineered) enzymes that are functional and that are maintaining or enhancing biological activity compared to the native or wild-type protein. Enzymes within the scope of the present disclosure may include, but are not limited to, pullulanases, proteases, cellulases, amylases, isomerases, lipases, oxidases, oxidoreductases, hydrolases, aldolases, ketolases, glycosidases, oxidoreductases, hydrolases, aldolases, ketolases, glycosidases, lyases, ligases, transferases, ligases, alcohol oxidase, and phenylalanine ammonia lyase.

The term "active site" refers to a part of an enzyme where substrates bind and undergo a chemical reaction. The majority of enzymes may be proteins but RNA enzymes called ribozymes may also be included. The active site of an enzyme is usually found in a cleft or pocket that is lined by amino acid residues (or nucleotides in ribozymes) that participate in recognition of the substrate. Residues that directly participate in the catalytic reaction mechanism are called active site residues. In general, an active site of an enzyme refers to any or all of the following: (i) the portion of an enzyme sequence that binds to substrate, (ii) the conserved domain or portion of the enzyme sequence that binds to an inhibitor, (iii) the portion of the enzyme sequence that binds to the substrate.

Therapeutic agents may also include cellular ligands. The ligands may induce receptor-mediated endocytosis, such as potocytosis. Other examples of the ligands may include, without limitation, folate, enkephalin, insulin, nerve growth factor, luteinizing hormone, hormone analogs, human growth hormone, gonadotrophin releasing hormone, calcitonin, catecholamines receptor agonists, antagonists and inhibitors. Cytokines, growth factors and peptide hormones may also be used as the ligands which may includes, without limitation, epidermal growth factor, nerve growth factor, somatostatin, endothelin, interleukin-1, interleukin-2, tumor necrosis factor, parathyroid hormone, insulin like growth factor I and fragments thereof.

Therapeutic agents may also include hydrophobic molecules that may be encapsulated by the polymers of the present disclosure. Examples of such hydrophobic molecules may include, but are not limited to: abietic acid, aceglatone, acenaphthene, acenocournarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allylsulfide, alprazolam, aluminum bis(acetylsalicylate), ambucetamide, aminochlothenoxazin, aminoglutethimide, amyl chloride, androstenediol, anethole trithone, anilazine, anthralin, Antimycin A, aplasmomycin, arsenoacetic acid, asiaticoside, asternizole, aurodox, aurothioglycanide, 8-azaguanine, azobenzene; baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butlated hydroxyanisole, butylated hydroxytoluene; calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, cournachlor, coumaphos, coumithoate cresyl acetate, crimidine, crufomate, cuprobam, cyamemazine, cyclandelate, cyclarbamate cymarin, cypermethril; dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscournacetate, ethylhydrocupreine, ethyl menthane carboxamide, eugenol, euprocin, exalamide; febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furftiryl-5-isopropylbarbituric acid, fusaftmgine, glafenine, glucagon, glutethimide, glybuthiazole, griseofulvin, guaiacol carbonate, guaiacol phosphate, halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione; josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone; octaverine, oleandrin, oleic acid, oxazeparn, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phenthnethylbarbituric acid, phenytoin, phosalone, O-phthalylsulfathiazole, phylloquinone, picadex, pifarnine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate; quercetin, quinbolone, quizalofo-ethyl, rafoxanide, rescinnamine, rociverine, ronnel; salen, scarlet red, siccanin, simazine, simetride, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol; ursolic acid, valinomycin, verapamil, vinblastine, vitamin A, vitamin D, vitamin E, xenbucin, xylazine, zaltoprofen, and zearalenone.

The therapeutic agent may be conjugated to the HBP using a variety of methods and strategies known in the art. In one embodiment, conjugation may occur by chemical modifications through the functional groups on the hyperbranched polymer. In another embodiment, conjugation may be facilitated by inserting a linker moiety between the hyperbranched polymer and the therapeutic agent. In another embodiment, conjugation may occur by directly binding the hyperbranched polymer to the therapeutic agent without using any functional group or linker to facilitate the binding.

In one embodiment, when both the HBP and the therapeutic agent have functional groups capable of forming hydrogen bond, the therapeutic agent may be conjugated to the HBP by simply mixing them together. Applicants envision that a simple mixture will most likely provide less protective benefit than the conjuge formed from chemical bonds.

In one preferred embodiment, the therapeutic agent may be conjugated to the HBP by chemical bonding and chemical modifications.

The term "chemical modifications", as used herein, refers to numerous methods and reagents for coupling therapeutic agents to the presently disclosed HBPs. These methods and reagents are well known to those of ordinary skill in the art. For example, Table 1 lists representative suitable functional groups that may be present on a hyperbranched polymer to couple therapeutic agents. U.S. Pat. No. 6,303,752 to Olsen el al., which is incorporated by reference herein its entirety for all purposes, describes use of the functional groups listed in Table 1, among others, to couple linkers, polymers and proteins. These are only some examples of conjugation chemistries that may be applied for use in practicing the invention described. One skilled in the art will understand which type of conjugation chemistry is suitable to use based on the type of the therapeutic agent-polymer combination including, for example, protein-small molecule-polymer hybrids.

TABLE 1

Functional Group Pairs for Conjugation Chemistry

| Functional Groups: | Reacts With: |
|---|---|
| Ketone groups (such as aldehydes) | amino, hydrazido and aminooxy |
| Imide | amino, hydrazido and aminooxy |
| Cyano | hydroxy |
| Alkylating agents (such as haloalkyl groups and maleimide derivatives) | thiol, amino, hydrazido, aminooxy |
| Carboxyl groups (including activated carboxyl groups) | amino, hydroxy, hydrazido, aminooxy |
| Activated sulfonyl groups (such as sulfonyl chlorides) | amino, hydroxy, hydrazido, aminooxy |
| Sulfhydryl | sulfhydryl |
| His-tag (such as a 6-His tagged peptide or protein) | nickel nitriloacetic acid |

TABLE 1-continued

Functional Group Pairs for Conjugation Chemistry

| Functional Groups: | Reacts With: |
|---|---|
| Thiocyano | amino |
| Aldehyde | amino |
| 2,4-pentanedione | guanidine |

In addition to the exemplary coupling partners in Table 1, other reagents may also be used to couple therapeutic agents to a HBP. For example, azide-containing compounds may be coupled to other molecules via Staudinger ligation. Suitable reagents for Staudinger ligation may be prepared according to the methods disclosed by Saxon and Bertozzi in U.S. Pat. No. 6,570,040 (the '040 patent) and by Raines et al. in U.S. Patent Publication No. 20040087779 (the '779 publication). The '040 patent and the '779 publication are incorporated herein by reference in their entireties. Also, the coupling methods suitable for bonding the disclosed HBP to a therapeutic agent may also include, without limitation, amino-reactive acylating agents, such as isocyanates and isothiocyanates, which form stable urea and thiourea derivatives respectively. Examples of such compounds have been used for protein crosslinking as described by Schick, A. F. et al. in *J. Biol. Chem.* 1961, 236, 2477.

Active esters are particularly useful for preparing the disclosed conjugate compounds, such as nitrophenylesters or N-hydroxysuccinimidyl esters. Suitable reagents and conditions for acylating amino groups using active esters are described by Bodanszky, M. and Bodanszky, A.; The Practice of Peptide Synthesis; Springer Verlag, New York, 1994; and by Jones, J.; Amino Acid and Peptide Synthesis; 2nd ed.; Oxford University Press, 2002, both of which are incorporated herein by reference. Other suitable linkages formed using the reagents listed in Table 1 may include disulfide linkages, formed by the oxidative coupling of two sulfhydryl-containing molecules. Another exemplary coupling technique may employ a chelated nickel moiety, such as nickel nitriloacetic acid, which couples with His-tagged peptides and proteins, including His-tagged antibodies.

Additional techniques for coupling materials, including those having the functional groups listed in Table 1, are taught by R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; and G. T. Hermanson et al., (1993), "Immobilized Affinity Ligand Techniques", Academic Press, N.Y. Each of these publications is incorporated herein by reference.

Furthermore, peptides and proteins, including antibodies, may also be covalently coupled to a nanoconjugate. For example, a native chemical ligation technique, such as described by Kent et al. in Chemical protein synthesis by solid phase ligation of unprotected peptide segments. *J. Am. Chem. Soc.* 121, 8720-27 (1999), may be used, as those in the Staudinger ligation protocols.

The disclosed compositions and methods may also encompass using a linker moiety to couple a therapeutic agent to the HBP through a covalent or non-covalent bond. Examples of useful linkers may include, without limitation, (1) carboxylic acids from 2 to 10 carbons (for example, the linker derived from succinic anhydride that has 4 carbons), (2) amino acids (from one to 10 amino acids in length), (3) polyethylene glycols in the molecular weight range of 500 Daltons to 20 KDaltons. For example, the linker may form a covalent linkage on either the therapeutic agent or the hyperbranched polymer, or both, and thus form two or more reactive moieties connected by a spacer element. The presence of such a spacer may, for example, permit bifunctional linkers to react with specific functional groups within a molecule or between two different molecules, resulting in a bond between these two components and introducing extrinsic linker-derived material into the conjugate.

The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

Linker moieties used to connect a therapeutic agent to the HBP may also include oligomer or polymer moieties such as polyalkylene oxides. Examples of such polymers may include, without limitation, polyethylene glycols, ethylene glycol, propylene glycol, ethanolamine, ethylenediamine, oligomers and derivatives thereof. Other representative spacer elements include oligosaccharides and polysaccharides, such as polygalacturonic acid, glycosaminoglycans, heparinoids, cellulose, alginates, chitosans carrageenans, dextran, aminodextran; peptides, polyamino acids and esters thereof, as in homo- and co-polymers of lysine, glutamic acid and aspartic acid; and oligonucleotides. Such linkers may contain enzyme cleavage sites.

Coupling methods of binding a therapeutic agent directly to the HBP without use of a functional group or linker moiety may also be encompassed by the disclosed compositions and methods. For example, a protein may be directly bonded to the HBP. The binding may be covalent or non-covalent.

Although any HBP may be used for conjugation, in certain embodiments, the conjugation may be performed using a HBP having one or more carboxylic acid end groups, which can be readily conjugated with a protein or other therapeutic agent containing an amino moiety. Accordingly, in certain embodiments, the HBP is conjugated to the therapeutic agent by (1) introducing one or more carboxylic acid groups on the HBP, and (2) conjugating the therapeutic agent with the carboxylic-acid modified polymer.

Functional end groups attached to the linear and terminal units of HBPs may be conveniently end-capped with small organic molecules. Depending on the end-groups of the HBP, the conjugation chemistry may vary. In general, functional groups on a HBP may include without limitation amine groups, carboxylic acids, and hydroxyl groups.

If the end group is already a carboxylic acid group, no additional initial modification is necessary. Amino and hydroxyl groups may be converted to carboxylic acid groups using a variety of methods known in the art. For example, the HBP containing hydroxyl or amino end groups may be reacted with a cyclic anhydride, such as succinic anhydride. The cyclic anhydride will react with the amino or hydroxyl end group to form a carboxyl end group, as shown in Scheme A below. Cyclic anhydrides used in this method may include without limitation succinic anhydride, glutaric anhydride, maleic anhydride, and citraconic anhydride. Maleic anhydride and citraconic anhydride may be used to create degradable protein-polymer conjugates for controlled release of protein cargo.

Scheme A: Converting amino and hydroxyl end groups to carboxylic acid end groups. TEA is triethylamine.

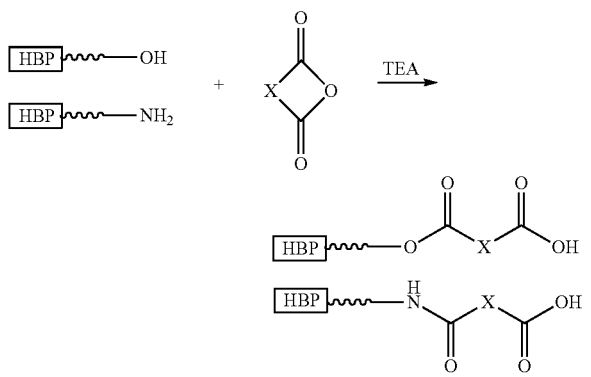

The chemistry of the second step (conjugating the therapeutic agent with the carboxylic-acid containing polymer) may be accomplished by procedures that are well known in the art. For example, the carboxylic acid groups generated in the first step may be conjugated to the amine groups on a protein or other therapeutic agent using EDC/NHS chemistry, as further illustrated in scheme B below. An amide linkage may be formed to conjugate the HBP to the therapeutic agent. EDC/NHS refers to the activation of the carboxylic acid with N-Hydroxysuccinimide (NHS), using ethyl(dimethylaminopropyl) carbodiimide (EDC) as a coupling agent.

Scheme B: Conjugating a carboxylic acid functionalized hyperbranched polymer (HBP) with a therapeutic agent having an amino moiety.

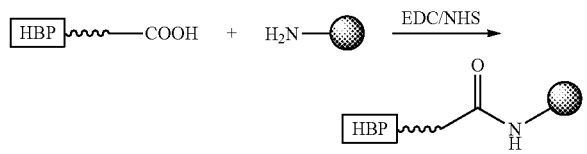

In a second aspect, the present disclosure encompasses a pharmaceutical composition that includes the conjugate as described previously and/or a pharmaceutically acceptable carrier.

As used herein, the term "pharmaceutical composition," refers to therapeutically effective amounts of the disclosed conjugate together with other suitable reagents. The other suitable reagents, collectively "pharmaceutically-acceptable carriers," may include any suitable diluents, preservatives, solubilizers, emulsifiers, bases, delivery vehicles, and adjuvants.

Pharmaceutical compositions may be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc., or onto liposomes, microemulsions, micelles, milamellar or multilamellar vesicles, erythrocyte ghosts, or spheroplasts. Such compositions may influence the physical state, solubility, stability, rate of in vive release, and rate of in vivo clearance. Controlled or sustained release compositions may include formulation in lipophilic depots (e.g., fatty acids, waxes, oils).

Also encompassed by the disclosure are methods of administering particulate compositions coated with additional polymers (e.g., poloxamers or poloxamines). Other embodiments of the compositions may incorporate particulate forms, including forms for oral rectal, and transmucosal delivery. In one embodiment, the pharmaceutical composition may be administered orally, rectally or transmucosally.

Further, as used herein, "pharmaceutically acceptable carriers" may be aqueous or non-aqueous solutions, suspensions, and emulsions. Examples of non-aqueous solvents may include propylene glycol, polyethylene glycol, vegetable oils such as olive oil, and injectable organic esters such as ethyl oleate. Aqueous carriers may include, but not limited to, water, alcoholic/aqueous solutions, emulsions or suspensions, e.g., saline and buffered media. Controlled or sustained release compositions, which are administrable according to the disclosure, may include formulation in lipophilic depots (e.g. fatty acids, waxes, oils). Other embodiments of the compositions administered according to the disclosure may incorporate particulate forms, protective coatings, protease inhibitors or permeation enhancers for various routes of administration, including transmucosal and oral.

The pharmaceutical preparation may comprise the conjugate alone, or may further include a pharmaceutically acceptable carrier, and may be in solid or liquid form such as tablets, powders, capsules, pellets, solutions, suspensions, elixirs, emulsions, gels, creams, or suppositories, e.g., rectal and urethral suppositories. Pharmaceutically acceptable carriers may include gums, starches, sugars, cellulosic materials, and mixtures thereof.

The pharmaceutical preparations administrable by the present invention may be prepared by known dissolving, mixing, granulating or tablet-forming processes. For oral administration, the conjugates may be mixed with additives customary for this purpose, such as vehicles, stabilizers, or inert diluents, and the conjugates may be converted by customary methods into suitable forms for administration, such as tablets, coated tablets, hard or soft gelatin capsules, aqueous, alcoholic or oily solutions. Examples of suitable inert vehicles may be conventional tablet bases such as lactose, sucrose, or cornstarch in combination with binders such as acacia, cornstarch, gelatin; with disintegrating agents such as cornstarch, potato starch, alginic acid; or with a lubricant such as stearic acid or magnesium stearate.

Examples of suitable oily vehicles or solvents may include vegetable or animal oils such as sunflower oil or fish-liver oil. Preparations may be effected both as dry and as wet granules. The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection may also be prepared. The preparation may also be emulsified. The active therapeutic ingredient is often mixed with excipients which are pharmaceutically acceptable and compatible with the active ingredient. Suitable excipients may include, for example, water, saline, dextrose, glycerol, ethanol, or the like or any combination thereof.

In addition, the composition may contain minor amounts of auxiliary substances such as wetting or emulsifying agents, pH buffering agents which enhance the effectiveness of the active ingredient. In another embodiment of the invention, the active conjugate may be delivered in a vesicle, in particular a liposome (see Langer, 1990, Science 249: 1527-1533; Treat et al., 1989, in Liposomes in the Therapy of Infectious Disease and Cancer, Lopez-Berestein and Fidler (eds.), Liss: New York, pp. 353-365; Lopez-Berestein, ibid, pp. 317-327; see generally ibid).

In one aspect, the present invention discloses formulations for protecting a therapeutic agent including the conjugate as described previously and other suitable agents as appreciated by one skilled in the art.

In one embodiment, the formulations may include other suitable carriers or vehicles as appreciated by one skilled in the art. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials.

Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar, buffering agents such as magnesium hydroxide and aluminum hydroxide; alginic acid; pyrogen free water, isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator.

In another embodiment, the formulations may include other suitable absorption-promoting agents as appreciated by one skilled in the art. The suitable absorption-promoting agents may be selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacyl methyl sulfoxide, azone, sodium lauryl sulfate, oleic acid, and the bile salts, may be employed to enhance mucosal penetration of the conjugate. In additional aspects, surfactants (e.g., polysorbates) are employed as adjunct compounds, processing agents, or formulation additives to enhance intranasal delivery of the conjugate. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the conjugate from the vehicle into the mucosa.

In another embodiment, the formulations may include other suitable penetration-promoting agent as appreciated by one skilled in the art. For example, the formulations may include one or more penetration-promoting agents selected from sodium salicylate and salicylic acid derivatives (acetyl salicylate, choline salicylate, salicylamide, etc.); amino acids and salts thereof (e.g. monoaminocarboxlic acids such as glycine, alanine, phenylalanine, proline, hydroxyproline, etc.; hydroxyamino acids such as serine; acidic amino acids such as aspartic acid, glutamic acid, etc; and basic amino acids such as lysine etc—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts).

In a further aspect, the present disclosure may encompasses a method of administering a therapeutic agent to a subject. The method may include the steps of conjugating the therapeutic agent to a HBP using a method as discussed above or any other suitable method as appreciated by one skilled in the art, and orally, rectally or transmucosally administering a therapeutically effective amount of the resulting conjugate to the subject. The term "Oral delivery", as used herein, refers to delivery by mouth and subsequently to the gastrointestinal tract, where the conjugate is absorbed. The term "rectal administration," as used herein, refers to use the rectum as a route of administration for medication and other fluids, which are absorbed by the rectum's blood vessels, and flow into the body's circulatory system, which distributes the drug to the body's organs and bodily systems. The term "transmucosal delivery", as used herein, refers to administration methods that deliver the active conjugate to the surface of a mucus membrane, followed by absorption of the conjugate through the mucus membrane. Transmucosal delivery may encompasse nasal, buccal/sublingual, vaginal, ocular and rectal delivery methods. Further details of oral and transmucosal delivery are provided above.

In another aspect, the present disclosure encompasses a method for making a conjugate for the oral, rectal or transmucosal delivery of a therapeutic agent to a subject. The method may include the step of conjugating a therapeutic agent to a HBP, whereby a conjugate is formed. Further details of this method are provided above and in the example below.

The following examples are offered for illustrative purposes only, and are not intended to limit the scope of the present invention in any way. Indeed, various modifications of the disclosed method in addition to those shown and described herein will become apparent to those skilled in the art from the foregoing description and the following examples and fall within the scope of the appended claims.

Examples pH-Sensitive Hyperbranched Polyglycerol-Based Protein Nanoconjugates Introduction Compared with current techniques for oral protein delivery, the inventive approach described here addresses the stability concern for therapeutic proteins residing within the harsh environment of the GI tract. Specifically, pH-sensitive hyperbranched polyglycerol (HPG)-based protein nanoconjugates have been developed and described here. The nanoparticles are carboxylic-acid-functionalized hyperbranched polyglycerol (HPG) conjugated with proteins. These nanoparticles are pH sensitive. First, they form aggregates upon exposure to acidic environment. Thus, they are easily precipitated in the harsh pH environment of the stomach, making them highly resistant to acid degradation. Upon entry into the intestine, where the pH rises to 8, the nanoparticle aggregates re-dissolve into solution, becoming functional again. Although the nanoparticles disperse well in neutral to basic solutions, the polymer attached to the surface of the protein can still protect the interior protein from protease digestion.

The system demonstrated in this example has the following advantages over conventional methods known in the art. First, conjugation of proteins with HPG causes only minor loss of activity, because the bulky HPG molecules cannot access the catalytic active site buried inside the protein peptide chain. Second, the HPG-protein nanocomposites have nanoscale range particle sizes, suitable for potential transmucosal delivery options. Third, the hyperbranched polyglycerol (HPG) is non-toxic and biocompatible, and thus causes few side effects when administered orally. Fourth, the surface of the HPG-protein nanocomposite is readily engineered to bond any ligand, tag, or other functional moieties to the nanocomposite. Procedures, Results, and Discussion.

The nanocomposites described here were synthesized using a three-step process.

First, the HPG was synthesized (Scheme 1).

was slowly added at 95° C. After completion of the reaction, the polymer was twice precipitated from methanol solution into acetone and subsequently dried in vacuo. Polyglycerol was obtained as a transparent, highly viscous liquid.

Functionalization of hyperbranched polyglycerol (HPG).

To an ice-cooled mixture of 0.4 g of polyglycerol (M~8000, 5 mmol of free OH groups) and 0.9 mL of triethylamine (6.5 mmol) dissolved in 15 mL of DMF, 500 mg of succinic anhydride (4.9 mmol) dissolved in 2 mL of DMF was added dropwise. The mixture was stirred overnight at room temperature. After the reaction was done, 6 M HCl was added to the mixture to neutralize it. Then, acetone was added and precipitants were collected, yielding carboxylic acid functionalized HPG-SA. To 10 mL DMF solution of the resulting precipitants, 0.57 g N-hydroxylsuccinimide, 1 g N,N'-dicyclohexylcarbodiimide (5 mmol) and 0.06 g 4-(Dimethylamino)pyridine (0.5 mM) were added. The solution was stirred at room temperature overnight. After the reaction was done, acetone was added and the precipitants were collected, yielding NHS activated HPG-SA-NHS.

Modification of PAL with HPG.

To 10 uL of 5 mg/mL PAL solution, 2 μL 10% HPG-SA-NHS was added. The mixture was stirred at 4° C. for 1 hour and dialyzed against 10 mM pH 7.4 Tris-HCl buffer containing 500 mM NaCl.

Confirming the Formation of the HPG-PAL Conjugate.

Gel electrophoresis was performed with both native PAL and the HPG-PAL conjugate synthesized according to our Scheme 1: Synthesis of hyperbranched polyglycerol (HPG)

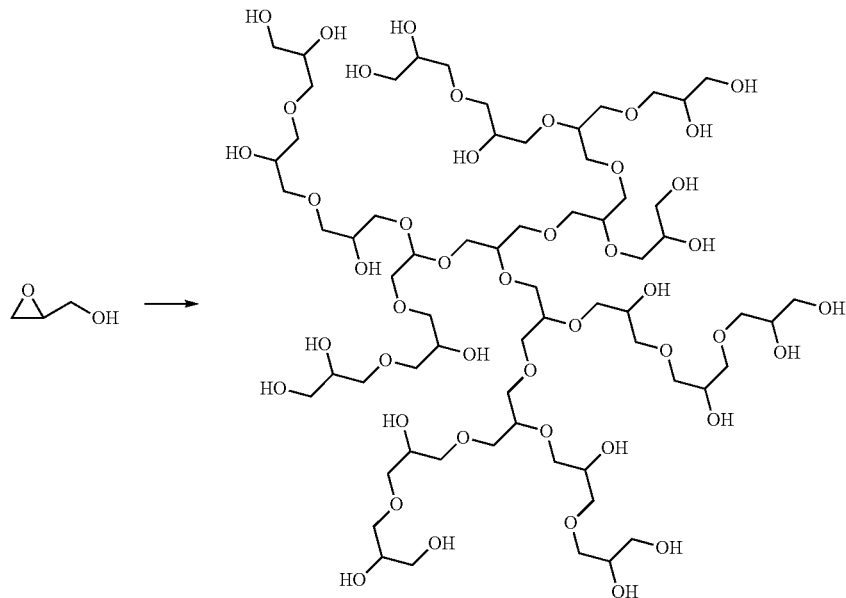

Figure 10:
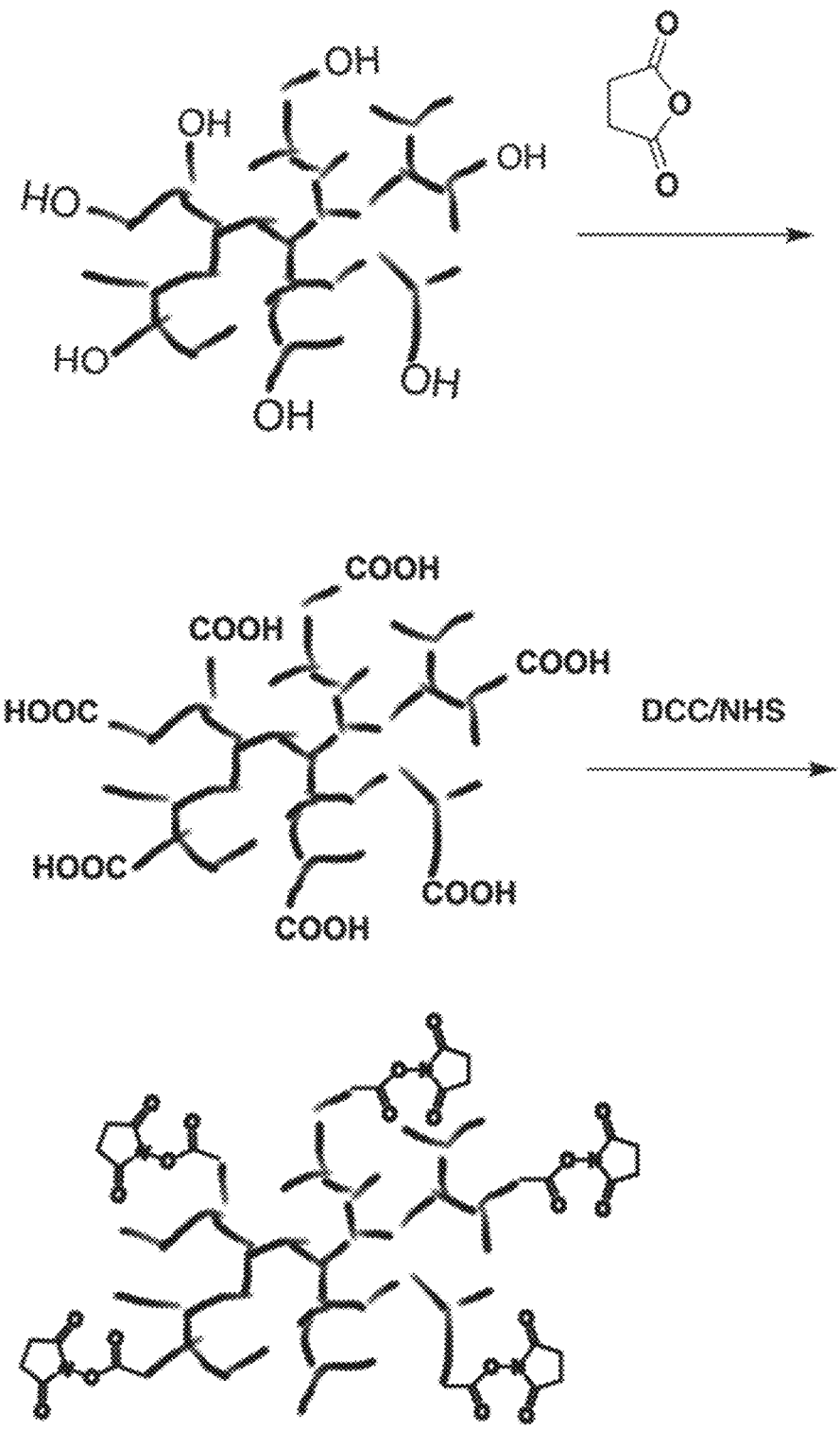
FIG. 10 depicts a synthetic scheme of carboxylic acid-functionalized HPG from HPG.

Second, the HPG was functionalized by the installation of carboxylate functional groups on the hydroxyl groups of the HPG according the method illustrated in Scheme 2 (FIG. 10).

Figure 11:
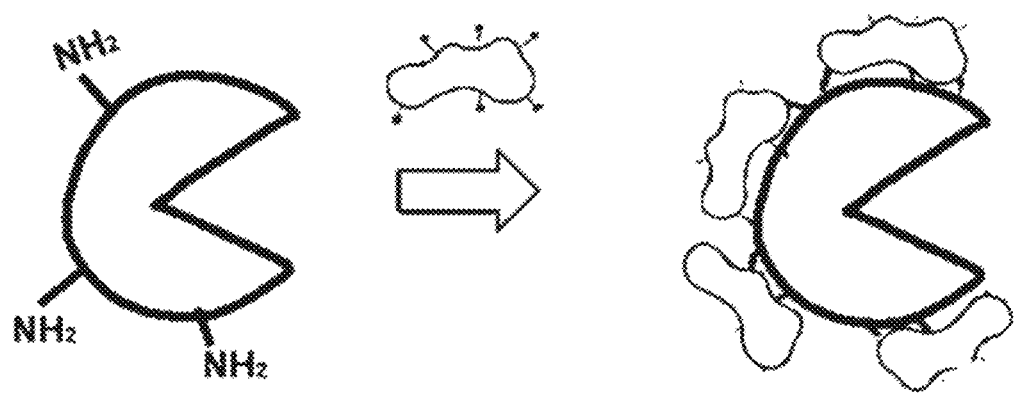
FIG. 11 depicts a conjugation of functionalized HPG to the protein.

Third, the functionalized HPG was conjugated according to the method illustrated in Scheme 3 (FIG. 11).

Preparation of Hyperbranched Polyglycerol (HPG).

Polymerizations were carried out in a reactor equipped with a stirrer and dosing pump under argon atmosphere. Glycerol was partially deprotonated (10%) with sodium ethylate solution (in ethanol). A 50 mL aliquot of glycidol procedure. The resulting image confirms the formation of the larger HPG-PAL conjugate (see FIG. 1).

Dynamic Light Scattering Measurement.

Figure 2:
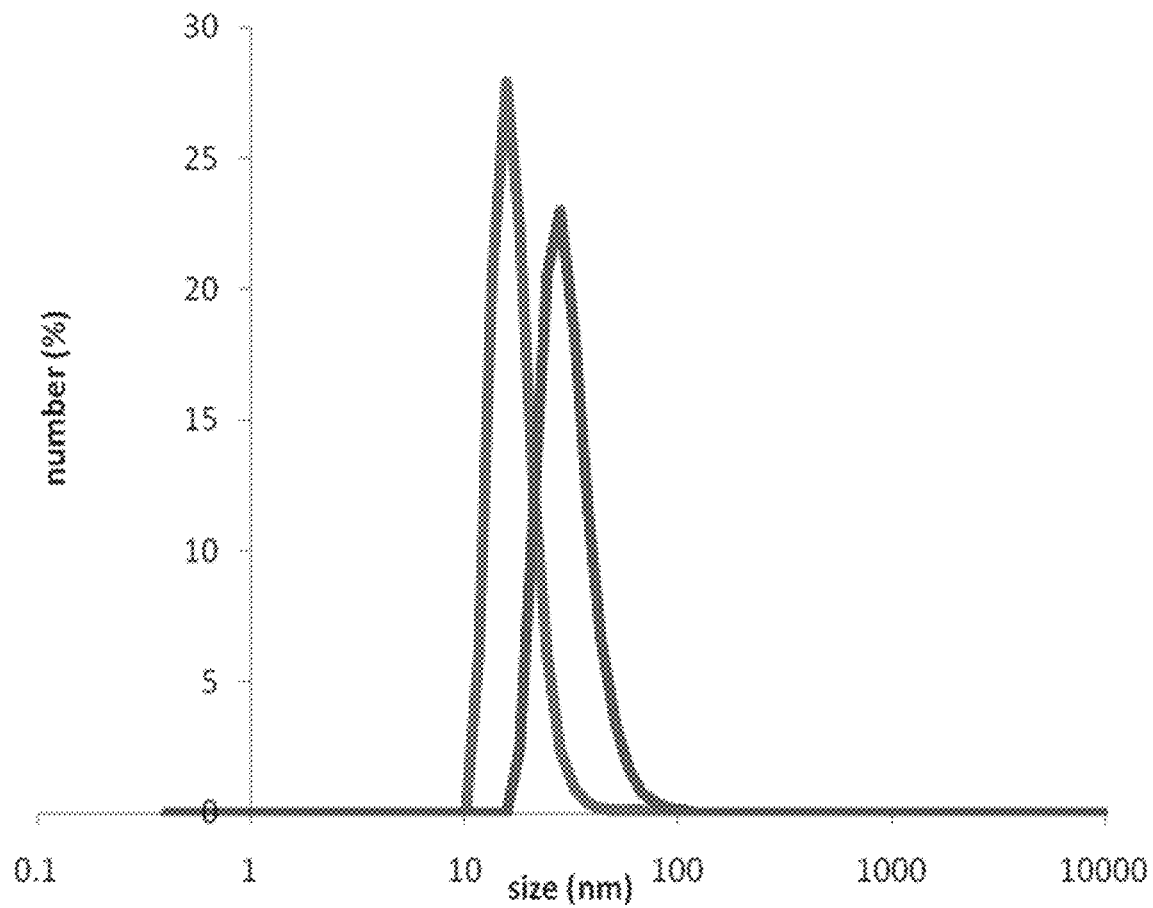
FIG. 2 is a graph showing the size distribution of native PAL (nPAL; darker leftmost peak) and of the PAL-hyperbranched polyglycerol (HPG) conjugate (HPG-PAL; lighter rightmost peak), as measured by dynamic light scattering.

To characterize the size increase after conjugating HPG with PAL, we conducted a dynamic light scattering measurement. 0.6 mL nanocapsule solution with a protein concentration of 1 mg/mL in pH 7.0 10 mM phosphate buffer in Malvern DTS 1060 capillary cells were placed in a Malvern Nano Zetasizer. Particle size was determined using a built-in refractive index for protein. As shown in FIG. 2, native PAL has a size around 12 nm (blue line); whereas after conjugation with PAL, the size increased to 50 nm, clearly indicating a successful conjugation of PAL with HPG.

Test of Enzymatic Activity.

In enzyme modification, there are two primary concerns that may prevent the modification from being successful. These are that the modification may either prevent the substrate from reaching the active site, or that the modification may prevent the enzyme from changing shape in the manner necessary to catalyze the reaction. Both of these situations would render the enzyme inactive and incapable of functioning as an active enzyme for its intended purpose.

To assess the activity of HPG-PAL, 10 µl of HGP-PAL was added to 300 µl of Phe in pH 7.8 Tris-HCl buffer. Because the byproduct of Phe degradation, trans-cinnamic acid, has light absorption at 290 nm, enzyme activity was determined with UV spectrophotometry over 1 minute. The process was then repeated with native PAL.

Figure 3:
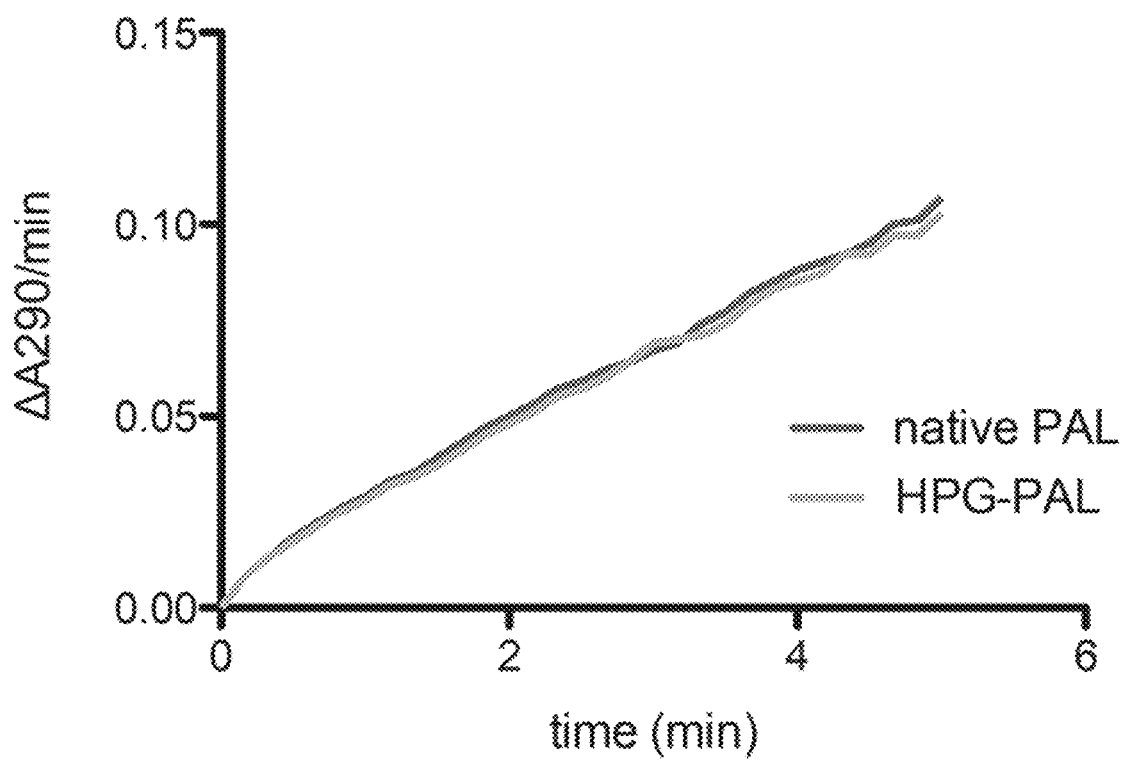
FIG. 3 is a graph showing change in absorption as a function of time for native PAL (darker line) and for HPG-PAL (lighter line) in pH 7.8 Tris-HCl buffer, as measured by UV spectrophotometry at 290 nm.

The initial test of activity showed that in control conditions, the enzymatic activity of HPG-PAL was very similar to the activity of native PAL (FIG. 3). This data demonstrates that modification with HPG does not reduce the activity of PAL.

Test of Robustness in Stomach Conditions (pH 2 and Pepsin).

This test was designed to expose the enzyme to the conditions of the human stomach. The human stomach is an environment that is inherently hostile to proteins, as its environment functions to digest proteins. There are two main characteristics of the stomach that would cause an enzyme to become inactivated. These are the presence of pepsin and the low pH.

Test the Resistance to Acid.

10 µl of HGP-PAL and native PAL were each incubated with 10 µl of pH 2 Glycine-HCl buffer for 30 minutes at 37° C. 300 µl of Phe in pH 7.8 Tris-HCl buffer was added and activity was assessed with UV spectrophotometry at 290 nm over 1 minute.

To test the resistance to pepsin, 10 µl of HGP-PAL and native PAL were each incubated with 10 µl of pH 2 Glycine-HCl buffer and 10 µl 0.1 mg/ml pepsin for 30 minutes at 37° C. 300 µl of Phe in pH 7.8 Tris-HCl buffer was added and activity was assessed with UV spectrophotometry at 290 nm over 1 minute.

Figure 4A:
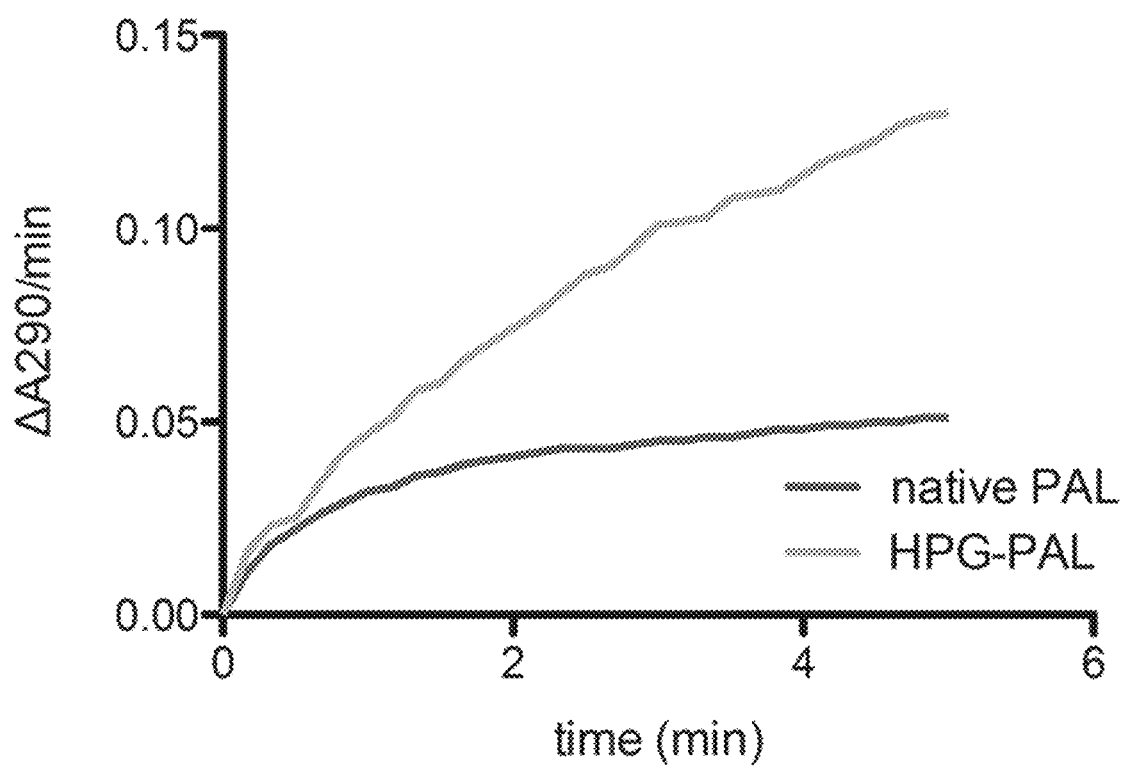
FIGS. 4A and 4B are graphs showing change in absorption of L-phenylanaline as a function of time when exposed to native PAL (lower, darker line) and HPG-PAL (higher, lighter line) after the PALs were incubated for 30 minutes at 37° C. in pH 2 Glycine-HCl buffer (FIG. 4A) or with pepsin in pH 2 Glycine-HCl buffer (FIG. 4B), as measured by UV spectrophotometry at 290 nm.
Figure 4B:
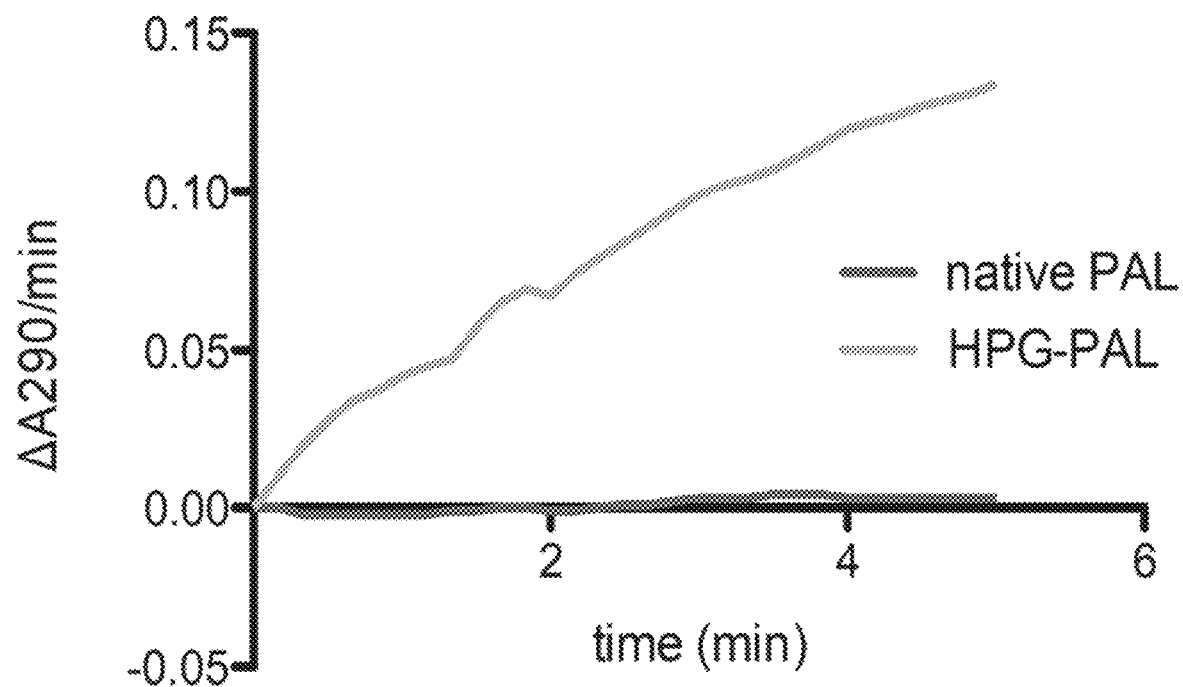

Native PAL displayed decreased activity when exposed to these conditions, while HPG-PAL maintained a high level of enzymatic activity (FIG. 4). This demonstrated that modification with HPG was able to protect PAL from being denatured by low pH and pepsin. Without being bound by any theory, HPG-PAL may be able to resist degradation by pepsin because HPG acts as a barrier to prevent the catalytic domain of pepsin from reaching the cleavage points on the amino acid chain of PAL. HPG-PAL may be able to resist the effects of low pH because it has been functionalized with carboxyl end groups.

Under acidic environment, the carboxyl groups are protonated; the HPG-PAL thus becomes hydrophobic. As a consequence, HPG-PAL precipitates into aggregates. These hydrophobic aggregates repel the external solution and protect the enzyme from being denatured by low pH. This effect also enhances the resistance to degradation by pepsin. When HPG-PAL is introduced to a less acidic solution, the carboxylic acid dissociates and becomes hydrophilic. Therefore, the HPG-PAL is dissolved well into solution.

Test of Robustness in Small Intestine Conditions (pH 8.5 and Trypsin).

This test was designed to expose the enzyme to the conditions of the small intestine. The small intestine is where a majority of protein digestion takes place, mostly due to the protease trypsin. To simulate the conditions in small intestine, 10 µl of HGP-PAL and native PAL were each incubated with 2 µl 1 mg/ml trypsin for 45 minutes at 37° C. 300 µl of Phe in pH 8.5 Tris-HCl buffer was added and activity was assessed with UV spectrophotometry at 290 nm over 1 minute.

Figure 5:
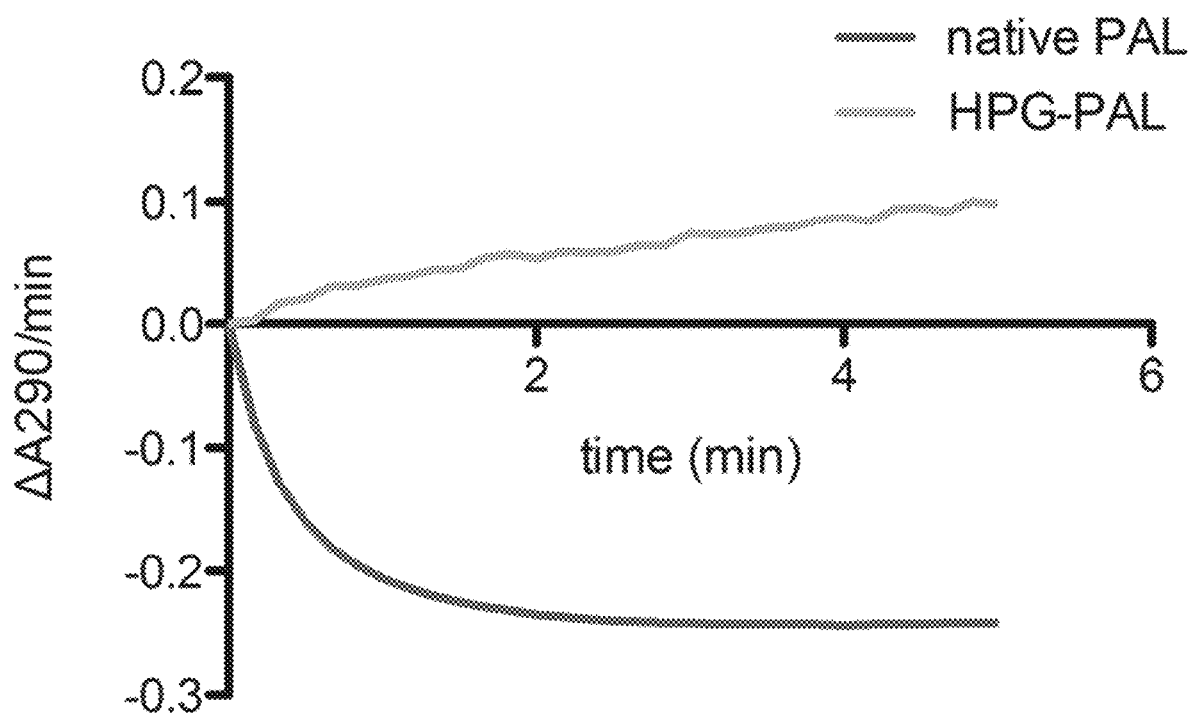
FIG. 5 is a graph showing change in absorption of L-phenylanaline as a function of time when exposed to native PAL (lower, darker line) and HPG-PAL (upper, lighter line) after the PALs were incubated for 45 minutes at 37° C. with trypsin and pH 8.5 Tris-HCl buffer.

After exposure to trypsin and pH 8.5, the enzymatic activity of native PAL was greatly reduced, while HPG-PAL maintained enzymatic activity (FIG. 5). As discussed previously, HPG acts as a barrier to prevent the catalytic domain of the protease trypsin from reaching cleavage points on PAL. This data shows that HPG-PAL displays increased activity over native PAL after exposure to pH 8.5 and trypsin.

Cell Viability Assay.

The purpose of this test was to determine if HPG-PAL would be cytotoxic to human cells. Cell viability was determined by resazurin assay. NIH/3T3 cells were seeded at a density of 5000/well in a 96-well plate the day before the experiment. 16 hours later, HPG-PAL with different concentrations was added into the cell medium and incubated for 24 hours. After the incubation, the medium was exchanged and resazurin was added to a final concentration of 0.01 mg/mL. The cells were incubated at 37° C. for another 3 hours with 405 nm excitation and 520 nm emission. Untreated cells and medium without cells were used as controls.

Figure 6:
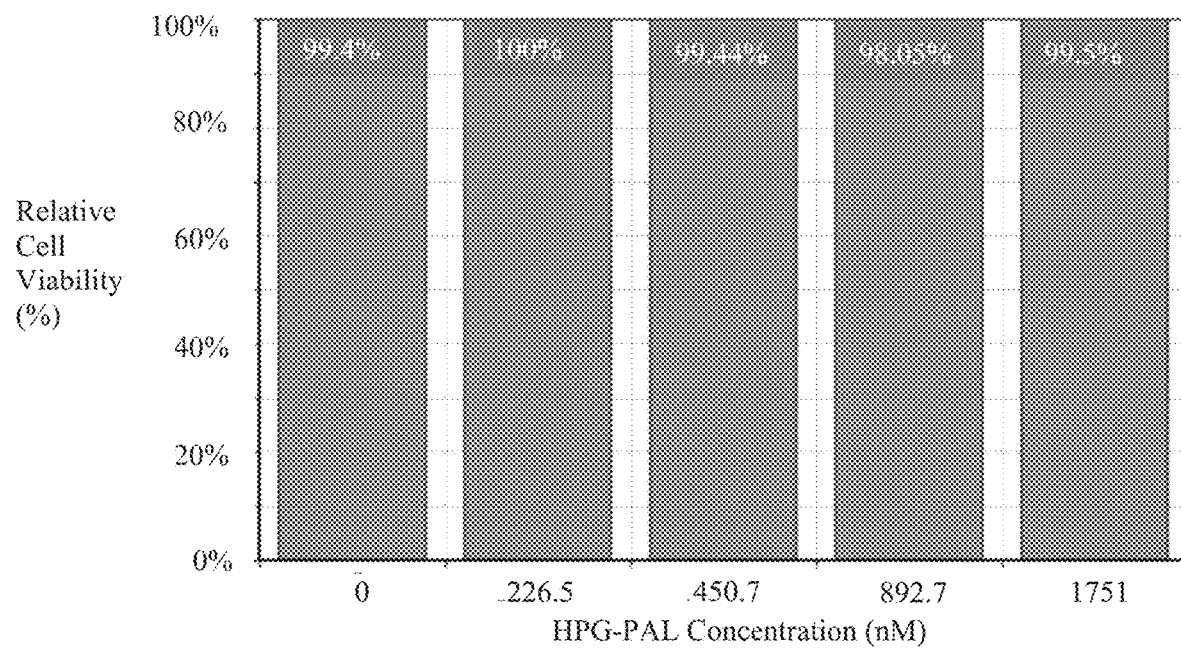
FIG. 6 is a bar graph showing cell viability as a function of the concentration of HPG-PAL present.

Out of the five concentrations tested, none caused significant cell death (FIG. 6). No relationship between HPG-PAL concentration and cell viability can be detected. Even at the highest concentration of 1751 nM, which is significantly higher than the concentration that would be used in a therapeutic formulation, no significant cell death was noted. This outcome was expected, as PAL and HPG are both relatively benign. In fact, HPG has already shown remarkably low cytotoxicity in vitro and in vive. This data shows that HPG-PAL is not toxic to human cells in therapeutic concentrations, and suggests that HPG-PAL will be safe for usage in vivo.

Figure 7:
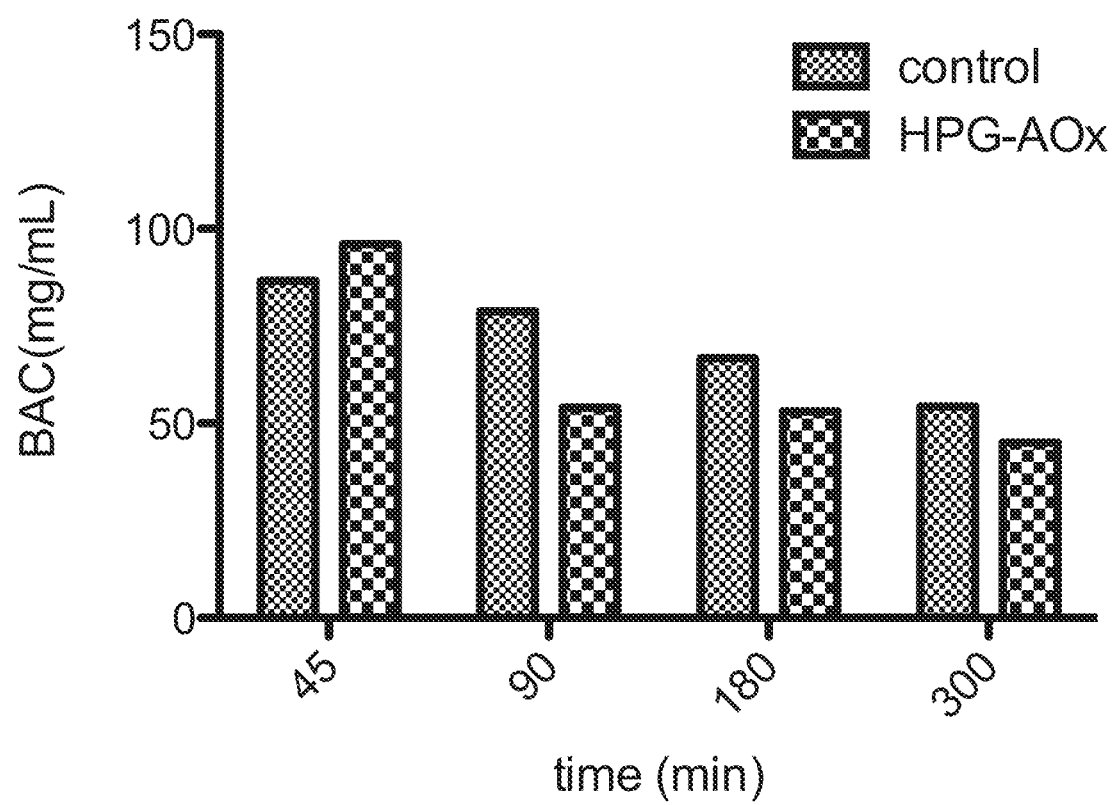
FIG. 7 is a bar graph showing mouse blood alcohol concentration as a function of time for both control mice fed an alcohol diet and for experimental mice fed with an alcohol+HPG-AOx diet.
Figure 8:
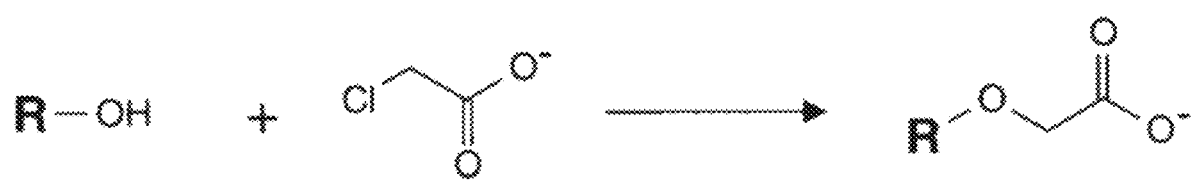
FIG. 8 depicts a synthetic scheme to convert hydroxyl group to carboxylate group. The reaction proceeds under basic conditions, yielding a stable ether bond terminating in a carboxymethyl group.
Figure 9A:
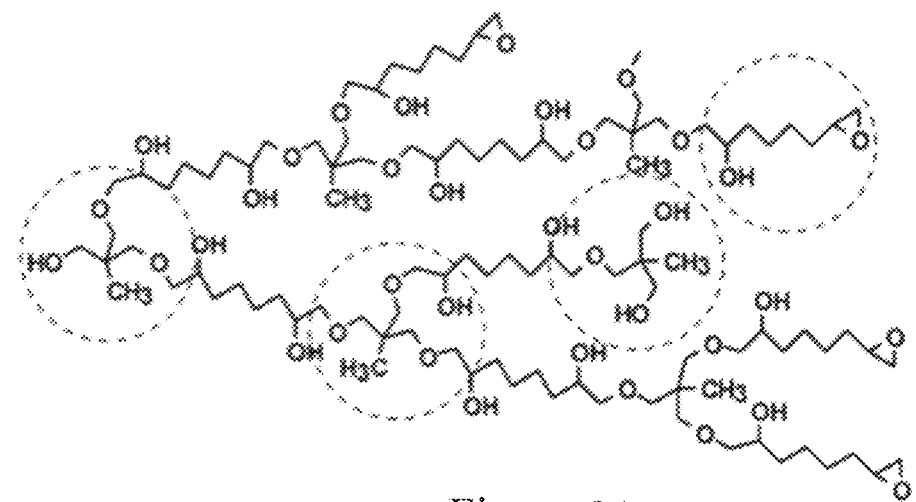
FIGS. 9A, 9B, 9C, 9D, 9E, 9F, 9G, 9H, 9I, 9J, 9K, 9L and 9M depict examples of additional polymers that could be functionalized to encapsulate biomolecules for oral delivery.
Figure 9B:
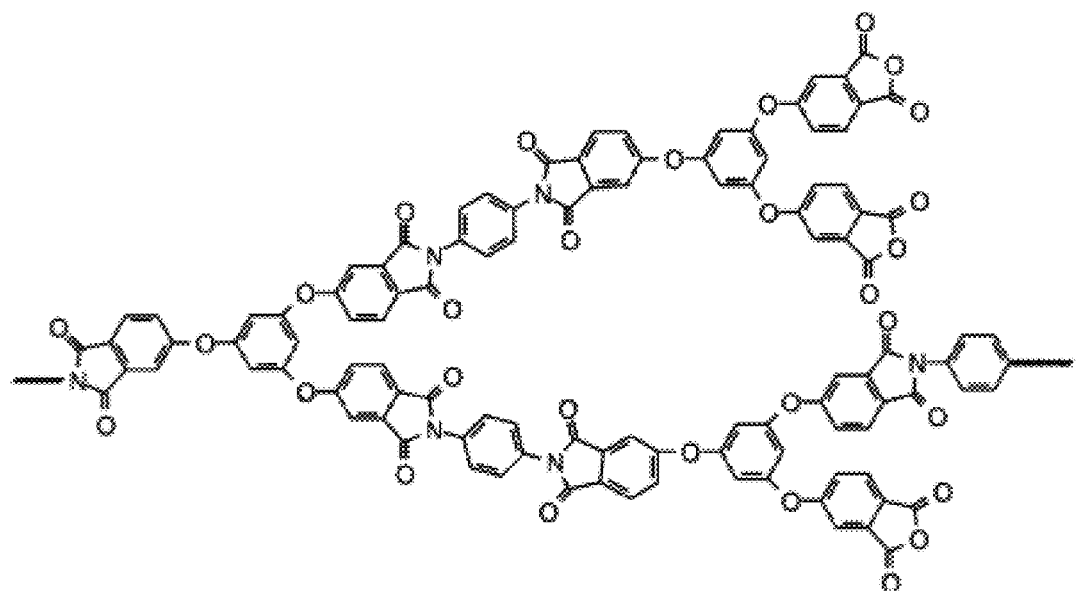
Figure 9C:
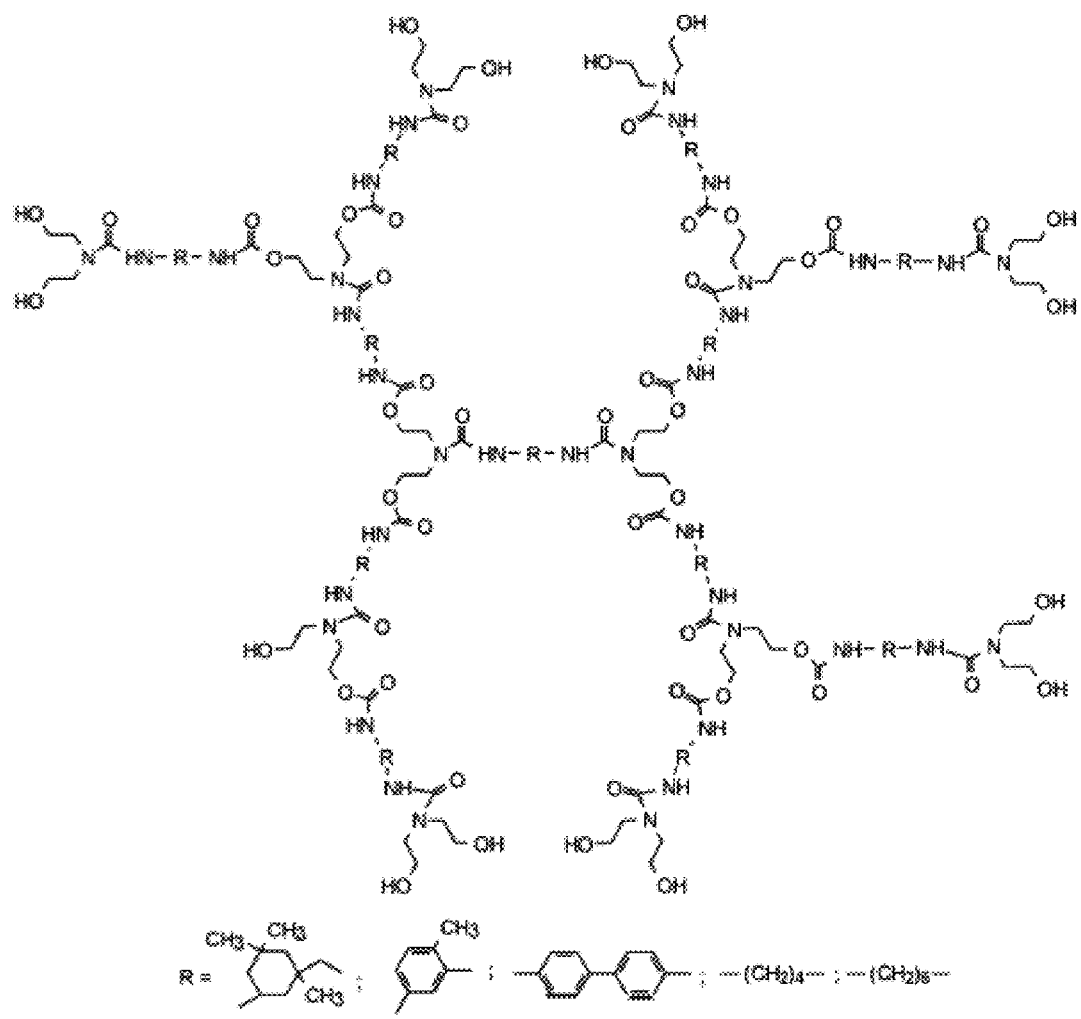
Figure 9D:
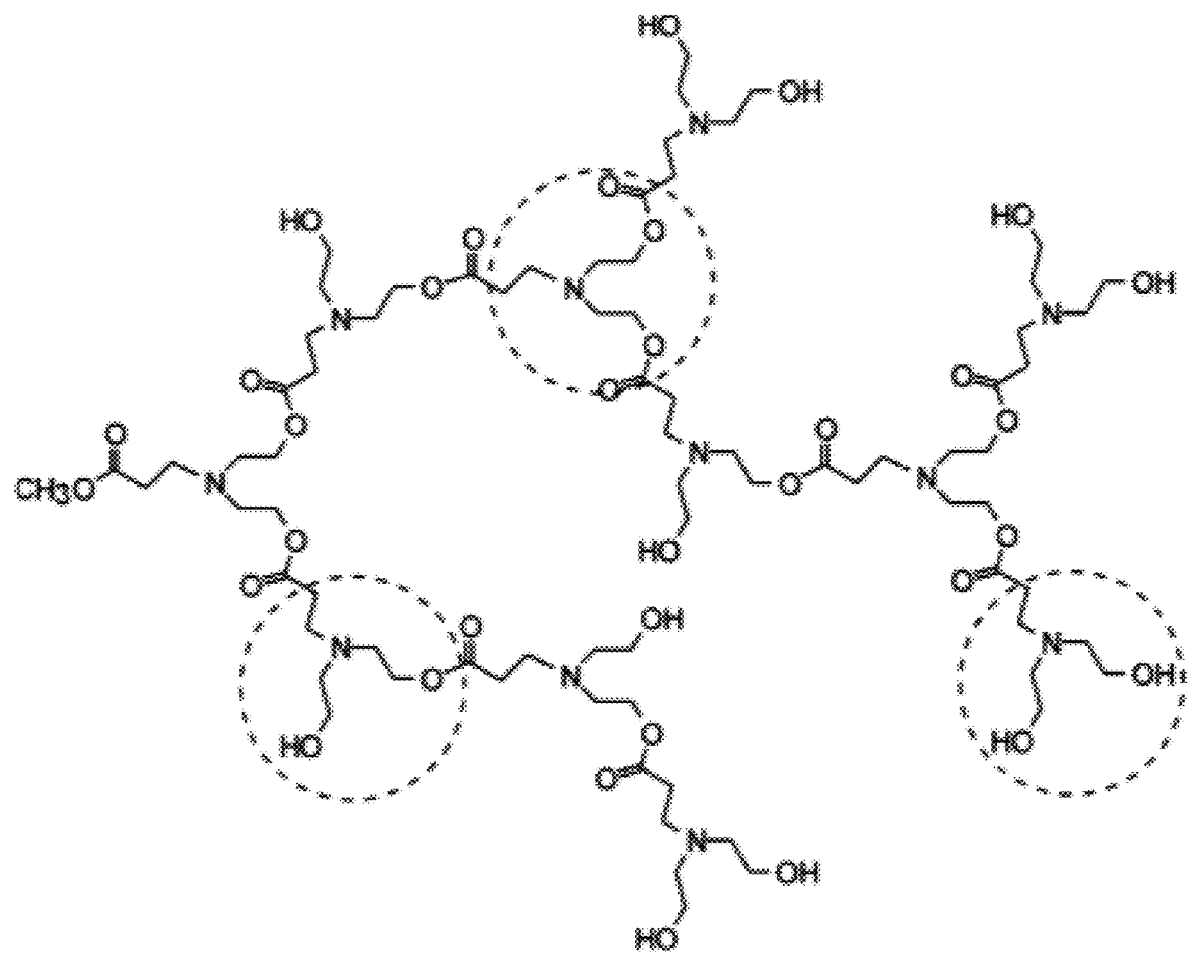
Figure 9E:
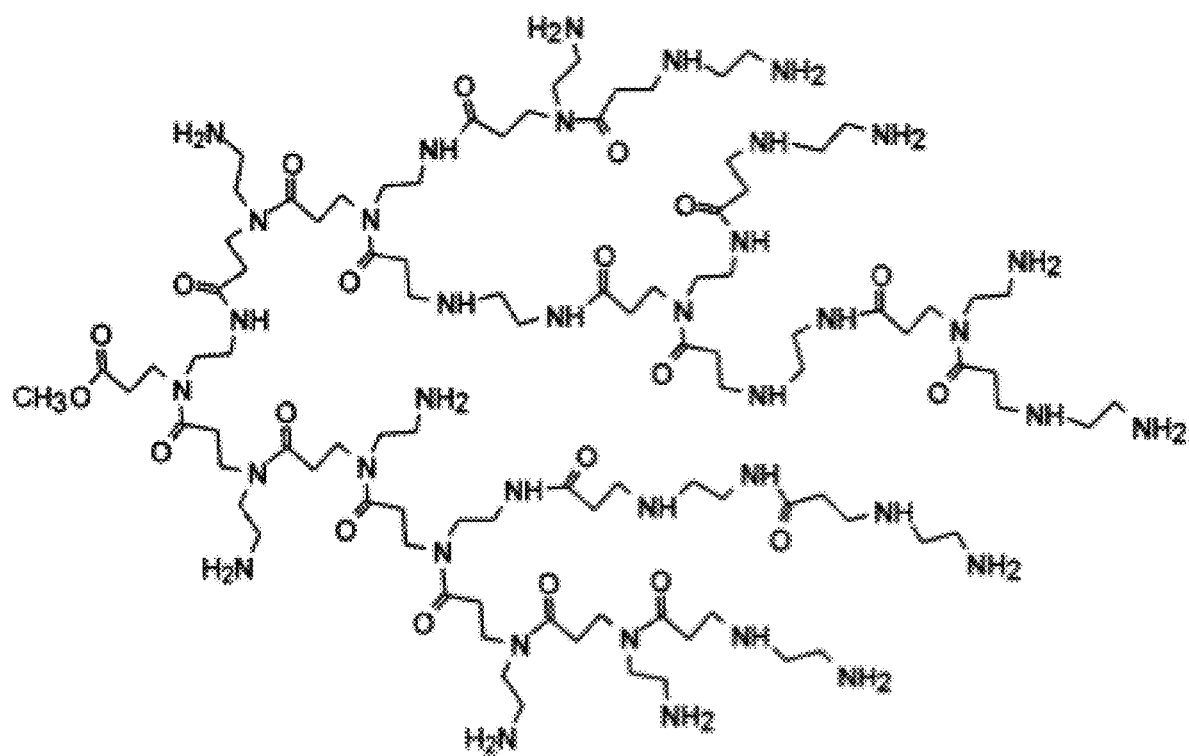
Figure 9F:
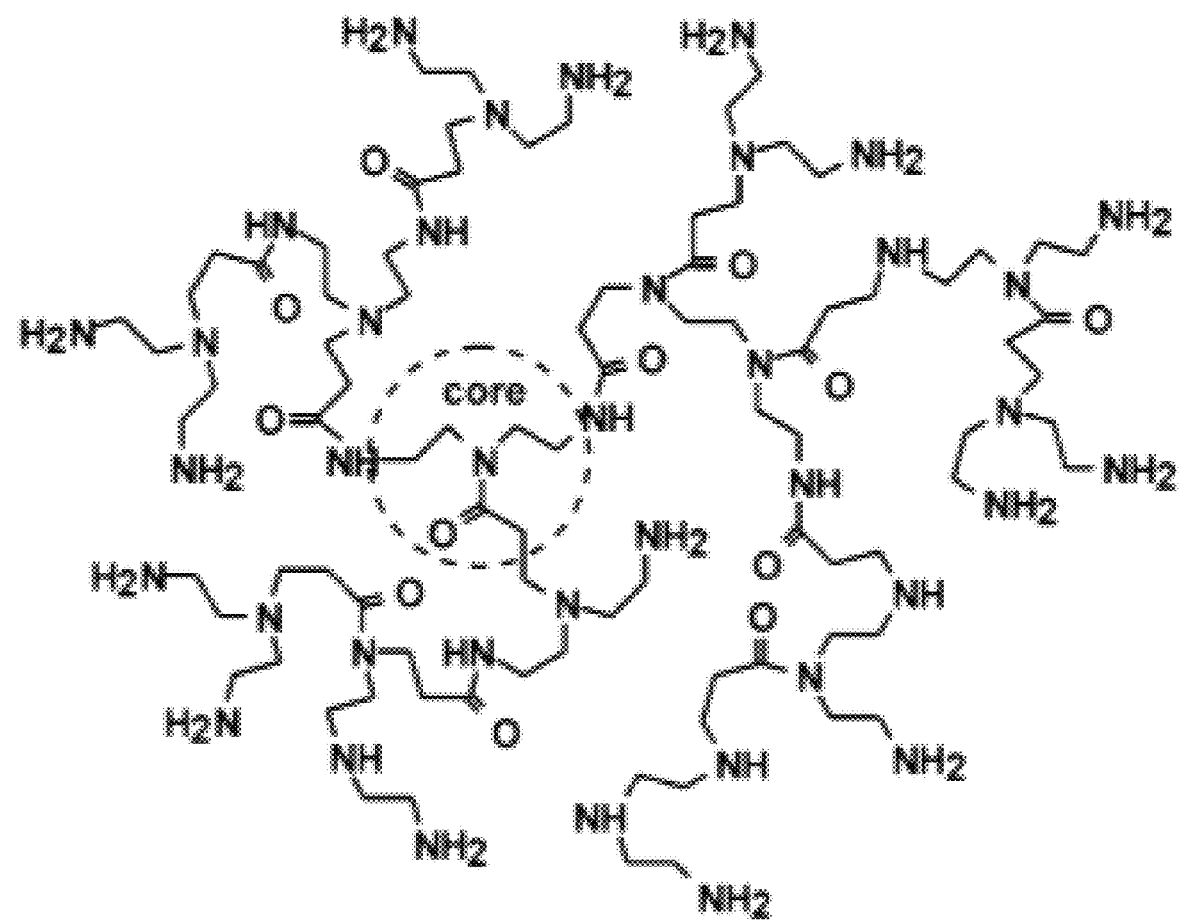
Figure 9G:
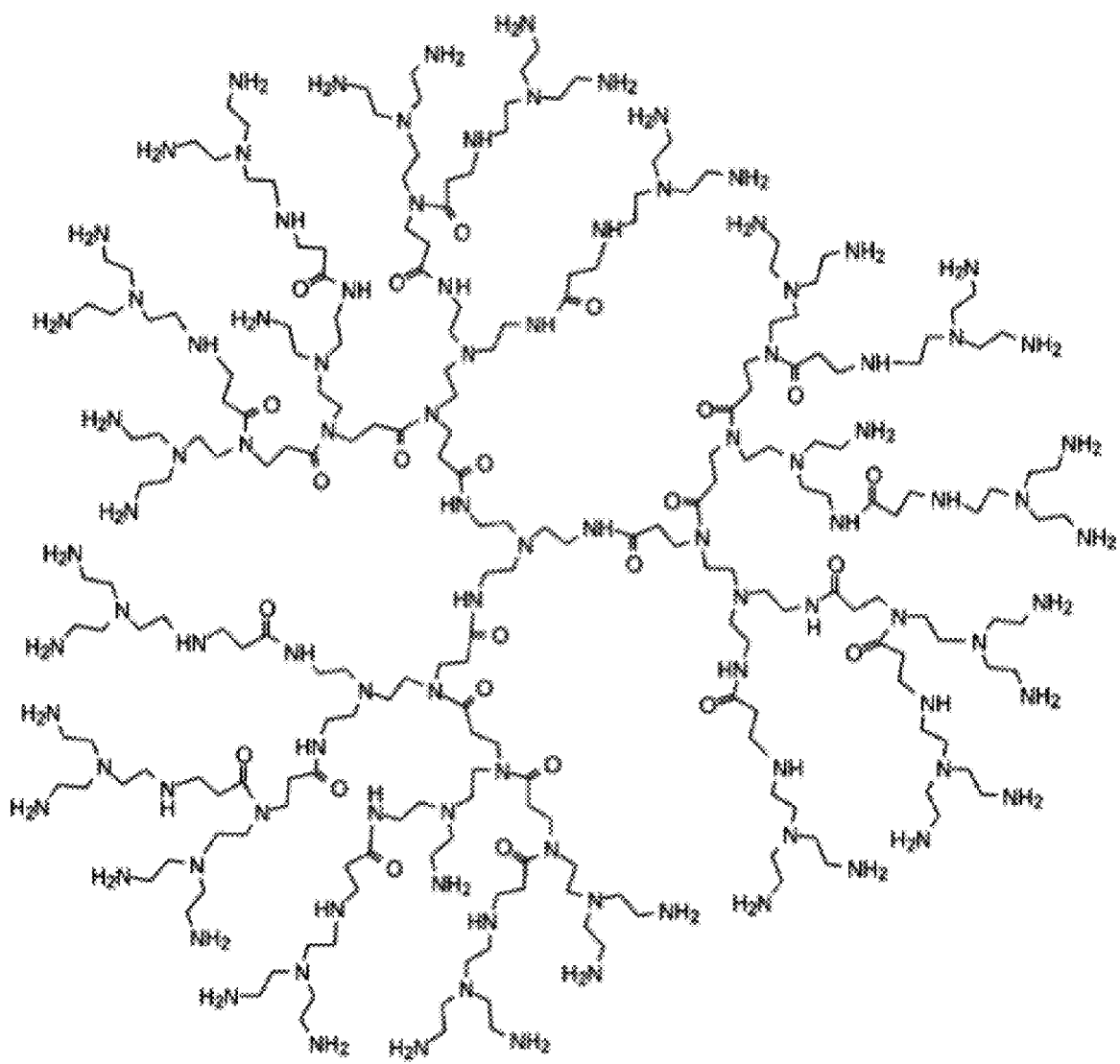
Figure 9H:
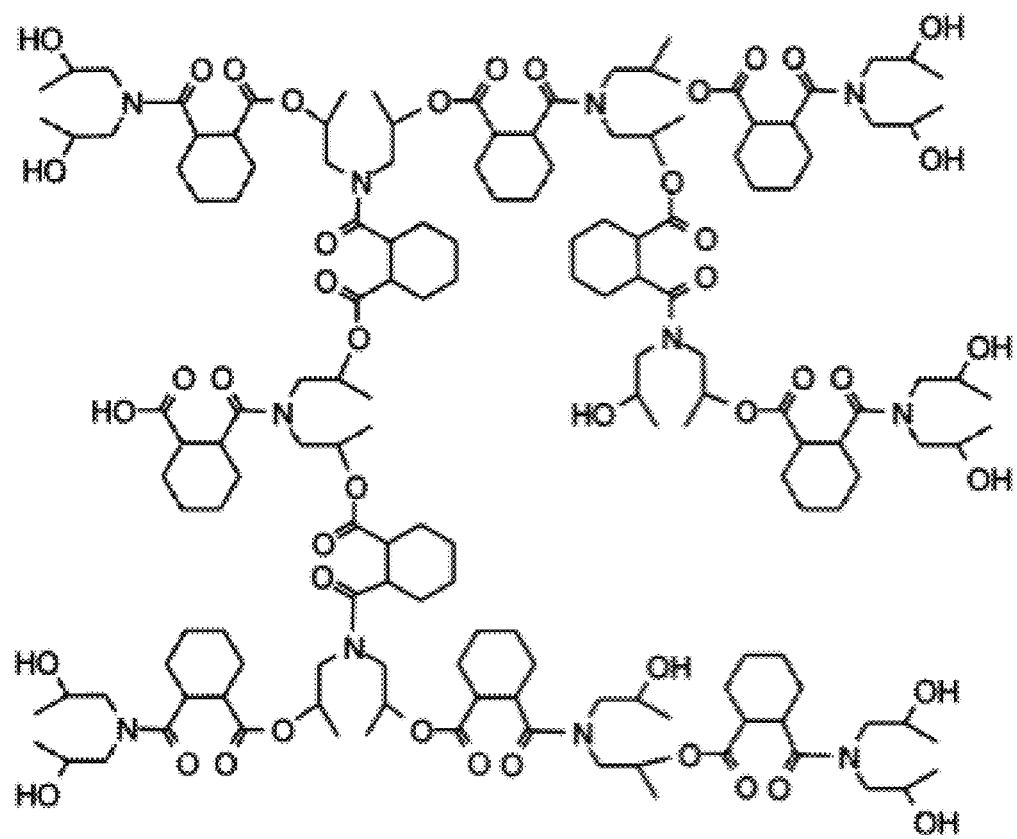
Figure 9I:
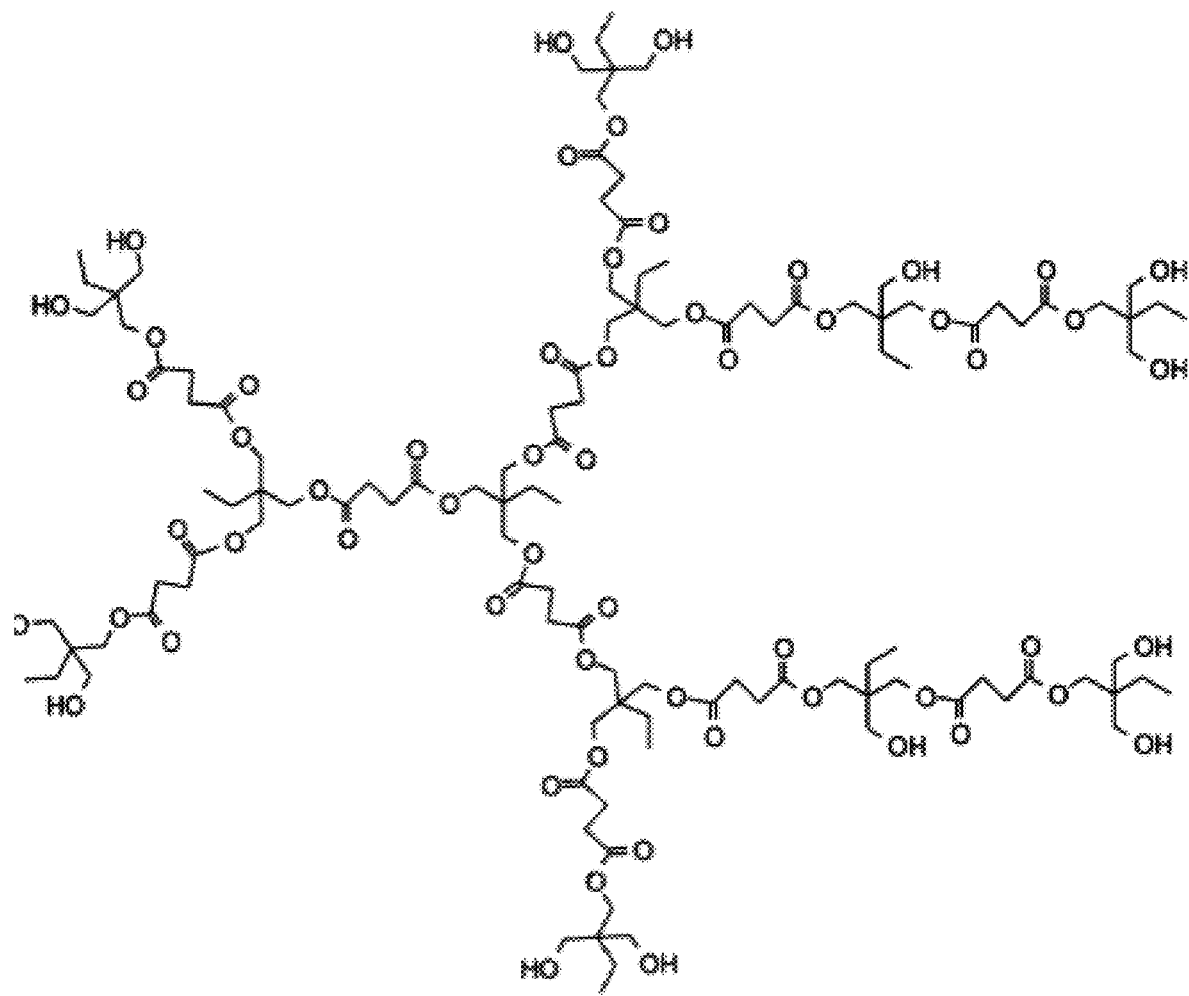
Figure 9J:
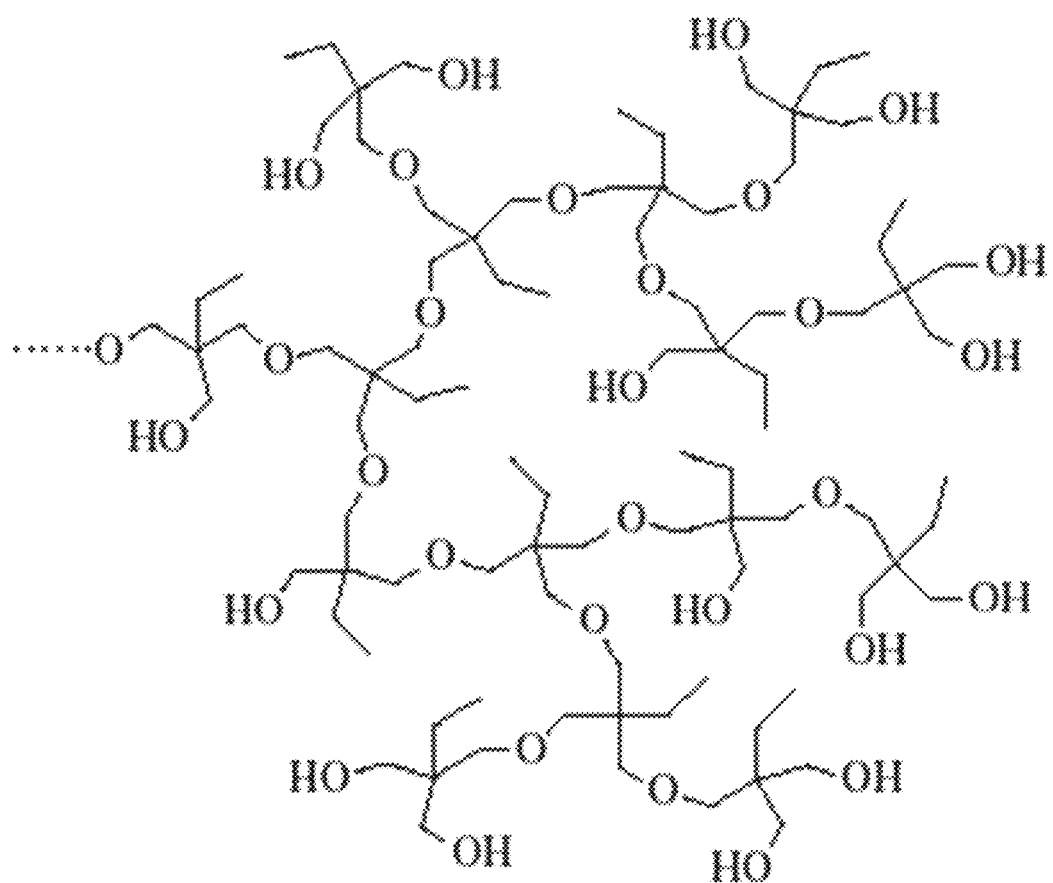
Figure 9K:
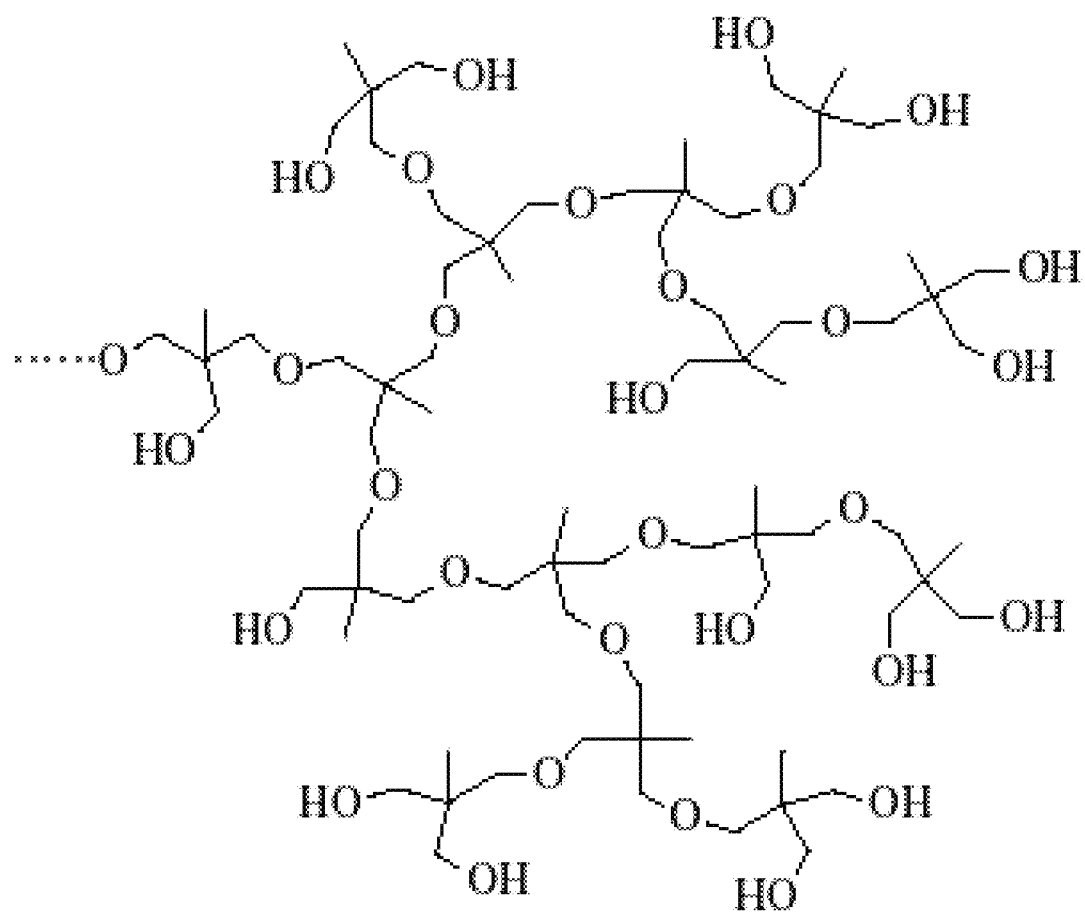
Figure 9L:
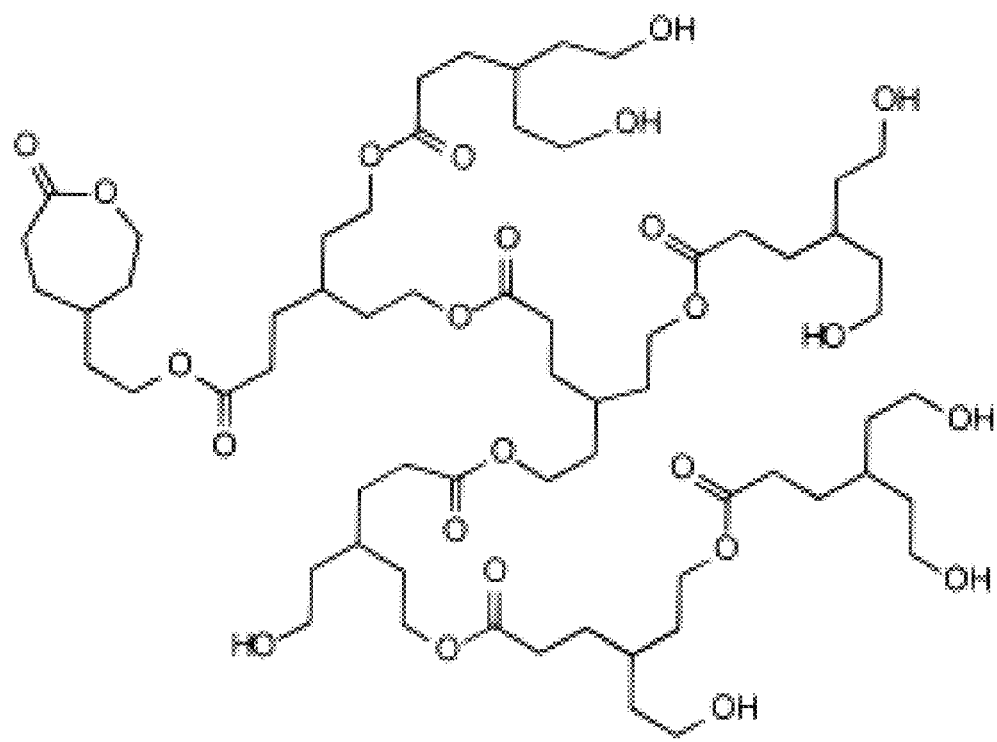
Figure 9M:
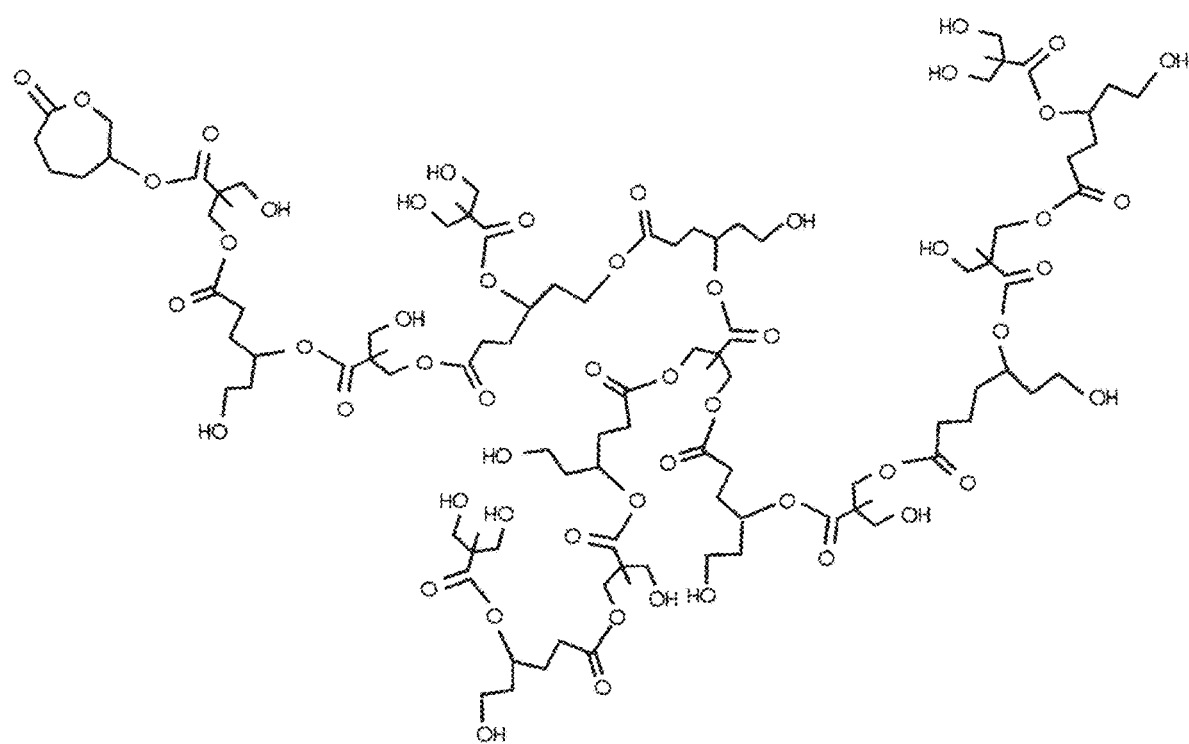

This method can be used in other enzymatic systems. We also fabricated HPG-conjugated alcohol oxidase (AOx) and applied it to blood alcohol removal in an in vive mouse model of alcohol abuse. In this set of experiments, mice were gavaged with an alcohol diet 48 hours after feeding them with HPG-PAL orally. The blood ethanol concentration (BAC) was monitored right after alcohol gavage for 5 hours. As shown in FIG. 7, there was a decreasing trend for BAC in both HPG-AOx treated mice and the control group during the 5 hours. However, HPG-AOx treated mice showed a comparatively lower BAC than control group at each time point, demonstrating the therapeutic effect of HPG-AOx.

CONCLUSION

These examples represent an important advancement in the enzyme-related oral therapeutics. For many years, proteolytic digestion has been a substantial issue preventing the successful oral delivery of therapeutic proteins. The demonstrated methods can be used for facilitating both oral and transmucosal delivery of therapeutic agents such as proteins.

Those skilled in the art will recognize, or be able to ascertain using no more than routine experimentation, numerous equivalents to the specific materials and methods described herein and in Appendix A. Such equivalents are considered to be within the scope of this invention and encompassed by the following claims.

We claim:

1. A conjugate for delivery of a therapeutic agent to a subject, comprising:
   (a) a therapeutic agent that comprises one or more amine moieties; and
   (b) a carboxylic acid modified hyperbranched polyglycerol (HPG) conjugated to the therapeutic agent by an amide linkage, wherein the therapeutic agent is a catalytically active enzyme or biomolecule selected from the group consisting of alcohol oxidase (AOx), phenylalanine ammonia lyase (PAL), insulin, calcitonin, an interferon, human growth hormone, a glucagon, gonadotrophin releasing hormone, encephalin, a vaccine, an enzyme, a hormone analog, an enzyme inhibitor, uricase, lactase, amylase, lipase, a protease, adenosine deaminase, L-asparaginase, and organophosphorous hydrolase, wherein the therapeutic agent and the HPG are conjugated in the presence of N-hydroxysuccinimide (NHS) and ethyl(dimethylaminopropyl) carbodiimide (EDC) to form the amide linkage.

2. The conjugate of claim 1, wherein delivery is selected from oral, rectal and transmucosal delivery.

3. The conjugate of claim 1, where the hyperbranched polyglycerol (HPG) is represented by a chemical structure selected from the group consisting of:

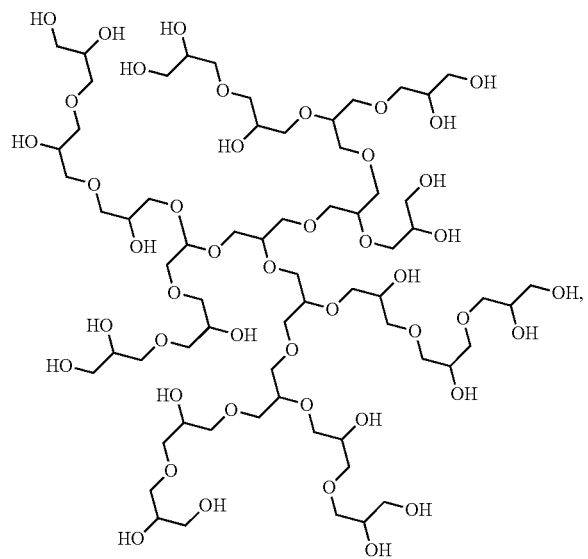

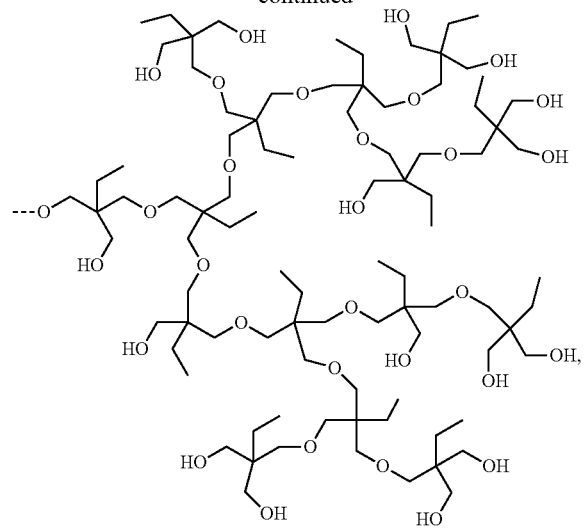

and

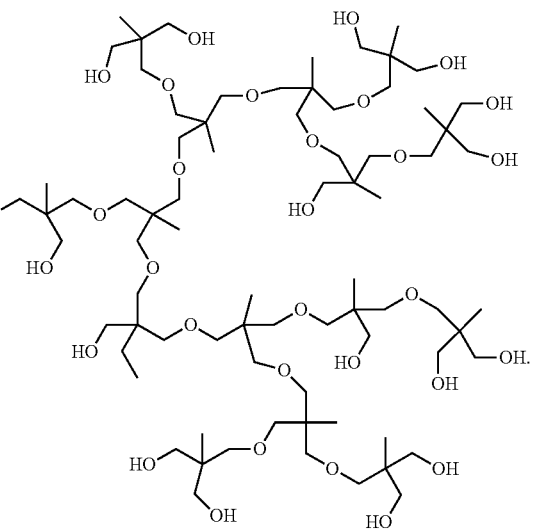

4. The conjugate of claim 1, wherein the therapeutic agent is a therapeutic protein.

5. The conjugate of claim 4, wherein the therapeutic protein is PAL or AOx.

6. The conjugate of claim 1, wherein a carboxyl group has been installed at one or more hydroxyl moieties of the HPG.

7. The conjugate of claim 6, wherein the carboxyl group is installed by contacting the one or more hydroxyl moieties with a cyclic anhydride.

8. The conjugate of claim 7, wherein the cyclic anhydride is succinic anhydride.

9. The conjugate of claim 1, wherein the therapeutic agent and the HPG are conjugated by contacting the carboxyl group with N-hydroxysuccinimide (NHS), whereby the carboxyl group is converted to an amine reactive N-hydroxysuccinimidyl carboxylate ester represented the formula

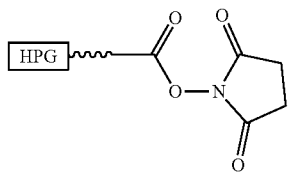

and wherein the amine reactive hydroxysuccinimidyl carboxylate ester conjugates with the one or more amine moieties on the therapeutic agent to form the amide linkage.

10. The conjugate of claim 1, wherein the conjugate is in the form of nanoscale particles of a size suitable for transmucosal delivery.

11. The protein conjugate of claim 10, wherein the conjugate is in the form of nanoscale particles that aggregate in an acidic environment and that remain dispersed in a neutral or basic environment.

12. A pharmaceutical composition comprising the conjugate of claim 1, and a pharmaceutically acceptable carrier.

13. A method of administering a therapeutic agent to a subject in need thereof comprising administering the conjugate of claim 1 to the subject.

14. The method of claim 13, wherein the administration of step (b) is selected from the group consisting of oral, rectal or transmucosal delivery.

15. The method of claim 13, wherein hyperbranched polyglycerol (HPG) is represented by a chemical structure selected from the group consisting of:

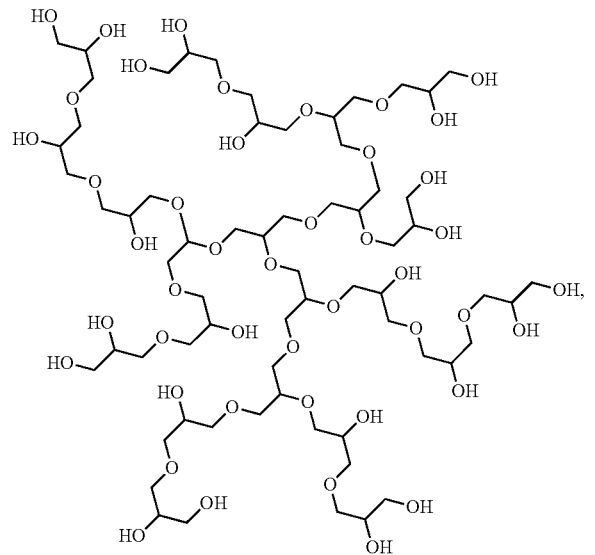

-continued

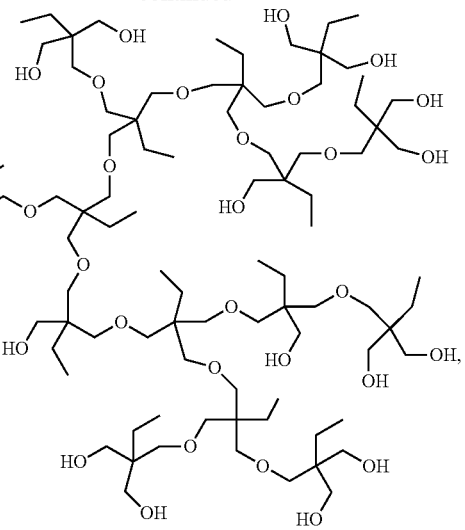

and

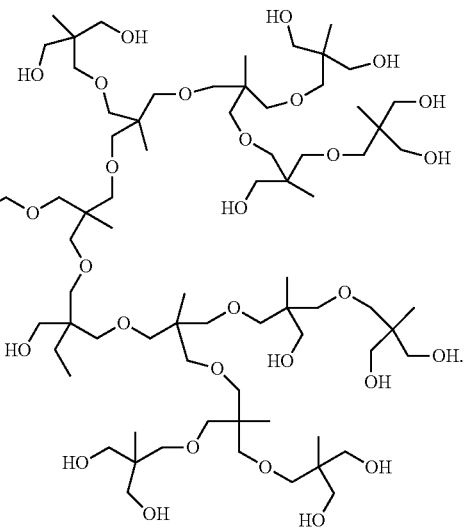

* * * * *

UNITED STATES PATENT AND TRADEMARK OFFICE
CERTIFICATE OF CORRECTION

PATENT NO. : 10,668,161 B2  
APPLICATION NO. : 15/120899  
DATED : June 2, 2020  
INVENTOR(S) : Yunfeng Lu et al.

Page 1 of 1

It is certified that error appears in the above-identified patent and that said Letters Patent is hereby corrected as shown below:

In the Specification

Column 27, Line 27, "(-C(-O)NH-C-)" should be --(-C(=O)NH-C-)--.

Column 27, Line 28, "(-N-CO)" should be --(-N=C=O)--.

Column 38, Line 5, "in vive" should be --in vivo--.

Column 44, Line 49, "in vive" should be --in vivo--.

Column 44, Line 58, "in vive" should be --in vivo--.

Signed and Sealed this  
Twenty-first Day of July, 2020

Andrei Iancu  
*Director of the United States Patent and Trademark Office*